(12) United States Patent
Coates et al.

(10) Patent No.: US 9,637,495 B2
(45) Date of Patent: May 2, 2017

(54) CGRP RECEPTOR ANTAGONISTS

(71) Applicant: Eli Lilly and Company, Indianapolis, IN (US)

(72) Inventors: David Andrew Coates, New Palestine, IN (US); Kevin Charles Fortner, Indianapolis, IN (US); Richard Duane Johnston, Greenfield, IN (US); Steven Marc Massey, Indianapolis, IN (US); Jason Kenneth Myers, Indianapolis, IN (US); Qing Shi, Carmel, IN (US); Miles Goodman Siegel, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/229,229

(22) Filed: Aug. 5, 2016

(65) Prior Publication Data

US 2017/0044163 A1 Feb. 16, 2017

Related U.S. Application Data

(60) Provisional application No. 62/266,769, filed on Dec. 14, 2015, provisional application No. 62/203,993, filed on Aug. 12, 2015.

(51) Int. Cl.
C07D 487/04 (2006.01)
C07D 471/04 (2006.01)
C07C 31/04 (2006.01)

(52) U.S. Cl.
CPC ............ *C07D 487/04* (2013.01); *C07C 31/04* (2013.01); *C07D 471/04* (2013.01); *C07B 2200/13* (2013.01)

(58) Field of Classification Search
None
See application file for complete search history.

(56) References Cited

U.S. PATENT DOCUMENTS

| 4,960,785 A | 10/1990 | Howard et al. |
| 2015/0203496 A1* | 7/2015 | Bell ..................... C07D 471/20 514/278 |

OTHER PUBLICATIONS

Pending U.S. Appl. No. 15/229,249, filed Aug. 5, 2016; Inventors: David Andrew Coates, Kevin Charles Fortner, Steven Marc Massey, Jason Kenneth Myers, Antonio Navarro, Miles Goodman Siegel; and Russell Dean Stucky; Applicant, Eli Lilly and Company.
Ohmatsu, Journal of the American Chemical Society, (2013), pp. 18706-18709, vol. 135, Issue 50.

* cited by examiner

*Primary Examiner* — Brian J Davis
(74) *Attorney, Agent, or Firm* — Nelsen L. Lentz

(57) ABSTRACT

The present invention provides a compound of Formula II:

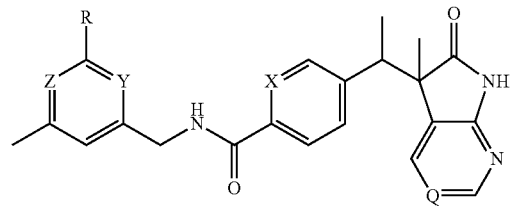

Formula II or a pharmaceutically acceptable salt thereof.

25 Claims, No Drawings

CGRP RECEPTOR ANTAGONISTS

The present invention relates to certain novel calcitonin gene-related peptide (CGRP) receptor antagonist compounds, to pharmaceutical compositions comprising the compounds, to methods of using the compounds to prevent or treat physiological disorders such as migraine, and to intermediates and processes useful in the synthesis of the compounds.

The present invention is in the field of prevention and treatment of migraine, and other neurological diseases and disorders thought to be mediated by CGRP (See for example, S. Benemei, et. al., *Current Opinion in Pharmacology,* 9, 9-14 (2009)). Migraine is a debilitating disease suffered by millions of people worldwide. Treatment options for migraine include the triptans, such as sumatriptan and zolmitriptan. Unfortunately, currently approved agents available to the patient do not always provide effective treatment, and these agents can be associated with various untoward side effects such as dizziness, paresthesia, and chest discomfort. In addition, triptans possess certain cardiovascular concerns causing them to be contraindicated in patients suffering from substantial underlying cardiovascular disease or uncontrolled hypertension (See T. W. Ho, et. al., *The Lancet,* 372, 2115-2123 (2008)). Thus, there is a significant unmet need in the prevention and treatment of migraine. CGRP antagonists are desired to provide more effective treatment for or prevention of certain neurological diseases, such as migraine.

U.S. Pat. No. 4,960,785 discloses certain 2-oxo-indoline compounds useful in therapy as aldose reductase inhibitors for the control of certain chronic diabetic complications. In addition, T. Ooi, et. al., *J Am. Chem. Soc.,* 135(50), 18706-18709 (2013) disclose an asymmetric substitution at the tetrasubstituted chiral carbon by way of a catalytic ring-opening alkylation of racemic 2,2-disubstituted aziridines with 3-substituted oxindoles.

The present invention provides certain novel compounds that are antagonists of the CGRP receptor. Furthermore, the present invention provides certain novel compounds that are antagonists of the CGRP receptor which have the potential for an improved side-effect profile in the treatment or prevention of migraine.

Accordingly, the present invention provides a compound of Formula II:

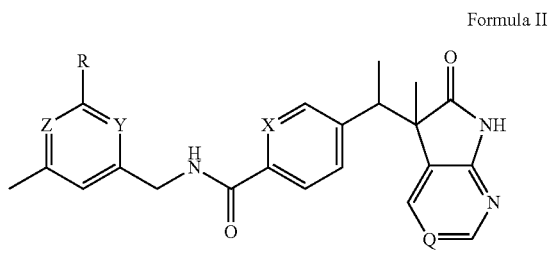

Formula II wherein
Y is CH or N
Z is CH or N;
provided that when Y is CH, Z is N and when Y is N, Z is CH;
X is CH or N;
Q is CH or N; and
R is C1-C3 alkyl, C3-C5 cycloalkyl, or CN;
or a pharmaceutically acceptable salt thereof.

The present invention further provides a compound of Formula I:

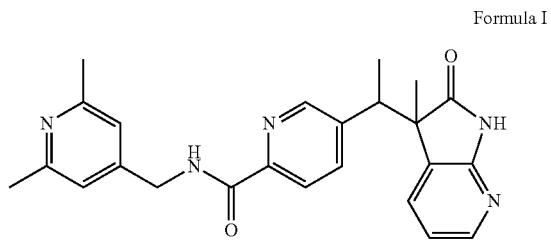 [SMILES: Cc1cc(CNC(=O)c2ccc(C(C)C3(C)C(=O)Nc4ncccc43)cn2)cc(C)n1]

Formula I or a pharmaceutically acceptable salt thereof.

The present invention also provides a method of preventing migraine in a patient, comprising administering to a patient in need thereof an effective amount of a compound of Formula I or Formula II, or a pharmaceutically acceptable salt thereof.

The present invention further provides a method of treating migraine in a patient, comprising administering to a patient in need thereof an effective amount of a compound of Formula I or Formula II, or a pharmaceutically acceptable salt thereof. The present invention also provides a method of antagonizing the CGRP receptor in a patient, comprising administering to a patient in need thereof an effective amount of a compound of Formula I or Formula II, or a pharmaceutically acceptable salt thereof.

Furthermore, this invention provides a compound of Formula I or Formula II, or a pharmaceutically acceptable salt thereof for use in therapy, in particular for the treatment of migraine. In addition, this invention provides a compound of Formula I or Formula II, or a pharmaceutically acceptable salt thereof for use in preventing migraine. Even furthermore, this invention provides the use of a compound of Formula I or Formula II, or a pharmaceutically acceptable salt thereof, for the manufacture of a medicament for the treatment of migraine or for preventing migraine.

The invention further provides a pharmaceutical composition, comprising a compound of Formula I or Formula II, or a pharmaceutically acceptable salt thereof, with one or more pharmaceutically acceptable carriers, diluents, or excipients. The invention further provides a process for preparing a pharmaceutical composition, comprising admixing a compound of Formula I or Formula II, or a pharmaceutically acceptable salt thereof, with one or more pharmaceutically acceptable carriers, diluents, or excipients. This invention also encompasses novel intermediates and processes for the synthesis of the compounds of Formula I and Formula II.

As used herein, the term "C1-C3 alkyl" refers to a methyl, ethyl, propyl and isopropyl group.

As used herein, the term "C3-C5 cycloalkyl" refers to a cyclopropyl, cyclobutyl, and cyclopentyl group.

As used herein, the terms "treating", "treatment", or "to treat" includes restraining, slowing, stopping, or reversing the progression or severity of an existing symptom or disorder.

As used herein, the term "preventing" or "prevention" refers to protecting a patient who is prone to a certain disease or disorder, such as migraine, but is not currently suffering from symptoms of the disease or disorder, such as symptoms of migraine.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I and Formula II, or pharmaceutically acceptable salts thereof are particularly useful in the prevention and treatment methods of the invention, but certain groups, substituents, and configurations are preferred. The following paragraphs describe such preferred groups, substituents, and configurations. Although the present invention contemplates all individual enantiomers and diasteromers, as well as mixtures of the enantiomers of said compounds, including racemates, the compounds with absolute configuration as set forth below are especially preferred. It is understood that these preferences are applicable both to the prevention and treatment methods and to the new compounds of the invention.

Compounds of Formula III:

Formula III

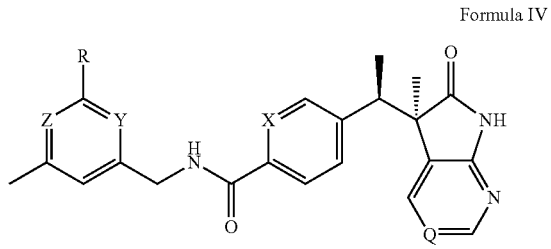

or pharmaceutically acceptable salts thereof are preferred.

Compounds of Formula IV:

Formula IV

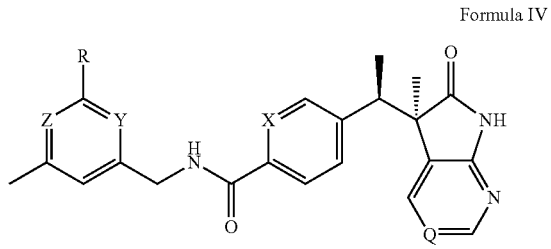

or pharmaceutically acceptable salts thereof, are further preferred. In addition, compounds or salts of Formulas I, II, III, and IV wherein Q is CH are preferred. Compounds or salts of Formulas I, II, III, and IV wherein Y is CH and Z is N are further preferred. The compounds or salts of Formulas I, II, III, and IV wherein R is C1-C3 alkyl are preferred with methyl being especially preferred.

The following compounds are more preferred:

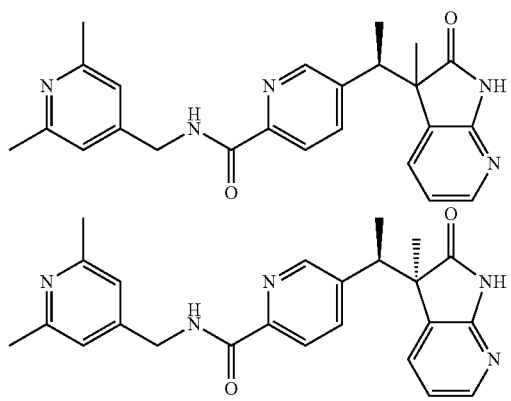

and the pharmaceutically acceptable salts thereof.

In addition, the following compound is particularly preferred:

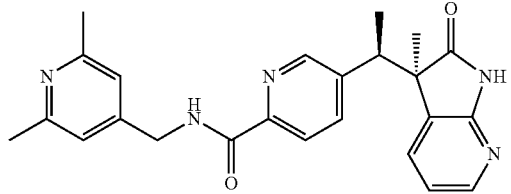 [SMILES: Cc1cc(CNC(=O)c2ccc([C@@H](C)[C@@]3(C)C(=O)Nc4ncccc43)cn2)cc(C)n1]

and the pharmaceutically acceptable salts thereof, with the HCl salt and free base being most especially preferred.

Moreover, the following HCl salt is even more preferred:

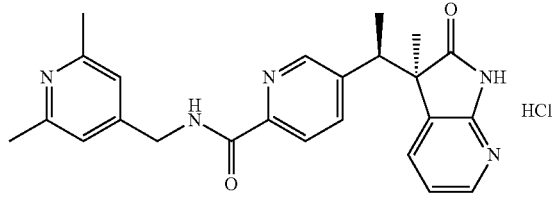 [SMILES: Cc1cc(CNC(=O)c2ccc([C@@H](C)[C@@]3(C)C(=O)Nc4ncccc43)cn2)cc(C)n1 ; Cl]

In addition, the hydrated form of the above HCl salt is especially preferred including the crystalline form of the above hydrated form of the HCl salt which is characterized by a substantial peak in the X-ray diffraction spectrum, at diffraction angle 2-theta of 20.7° in combination with one or more of the peaks selected from the group consisting of 19.8°, 12.9°, and 14.0°; with a tolerance for the diffraction angles of 0.2 degrees.

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Certain abbreviations are defined as follows: "ACN" refers to acetonitrile; "AcOH" refers to glacial acetic acid; "BOP" refers to (benzotriazol-1-yloxy)tris(dimethylamino)phosphonium hexafluorophosphate; "c-Bu" refers to cyclobutyl; "c-Pr" refers to cyclopropyl; "DCM" refers to dichloromethane or methylene chloride; "DIPEA" refers to N,N-diisopropylethylamine; "DMEA" refers to N,N-dimethylethylamine; "DMF" refers to N,N-dimethylformamide; "DMSO" refers to dimethylsulfoxide; "EDCI" refers to 1-ethyl-3-(3-dimethylaminopropyl)carbodiimide; "EDTA" refers to ethylenediamine tetraacetic acid; "EtOAc" refers to ethyl acetate; "Et" refers to ethyl; "EtOH" refers to ethanol; "HATU" refers to 1-[Bis(dimethylamino)methylene]-1H-1,2,3-triazolo[4,5-b]pyridinium 3-oxid hexafluorophosphate; "HPLC" refers to High Performance Liquid Chromatography; "HOAT" refers to 1-hydroxy-7-azabenzotriazole; "HOBt" refers to hydroxybenzotriazole; "hr" refers to hour or hours; "HTRF" refers to Homogeneous Time Resolved Fluorescence; "IC$_{50}$" refers to the concentration of an agent that produces 50% of the maximal inhibitory response possible for that agent; "i-Pr" refers to isopropyl; IPAm" refers to isopropylanine; "kPa" refers to kilopascal or kilopascals; "KO$^t$Bu" refers to potassium-tert-butoxide; "LAH" refers to lithium aluminum hydride; "LC-ES/MS" refers to Liquid Chromatography Electrospray Mass Spectrometry; "LDA" refers to lithium diisopropylamide; "LDI" refers to laser Doppler imaging; "min" refers to minute or minutes; "Me" refers to methyl; "MeOH" refers to methanol or methyl alcohol; "MTBE" refers to methyl-tert-butyl ether; "NHP" refers to non-human primate; "NMP" refers to N-methyl pyrrolidinone or 1-methyl pyrrolidinone; "psi" refers to pounds per square inch; "rpm" refers to revolutions per minute; "RT" refers to room temperature; "SEM" refers to standard error of the mean; "SFC" refers to supercritical fluid chromatography; "SNAR" refers to nucleophilic aromatic substitution reaction; "T3P" refers to 2,4,6-tripropyl-1,3,5,2,4,6-trioxatriphosphorinane-2,4,6-trioxide solution; "t-BuOH" refers to tert-butanol; "TEA" refers to triethylamine; "TFA" refers to trifluoroacetic acid; "THF" refers to tetrahydrofuran; "t$_R$" refers to retention time; "U/mL" refers to units per milliliter.

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, examples, and assays further illustrate the invention, but should not be construed to limit the scope of the invention in any way.

Scheme 1

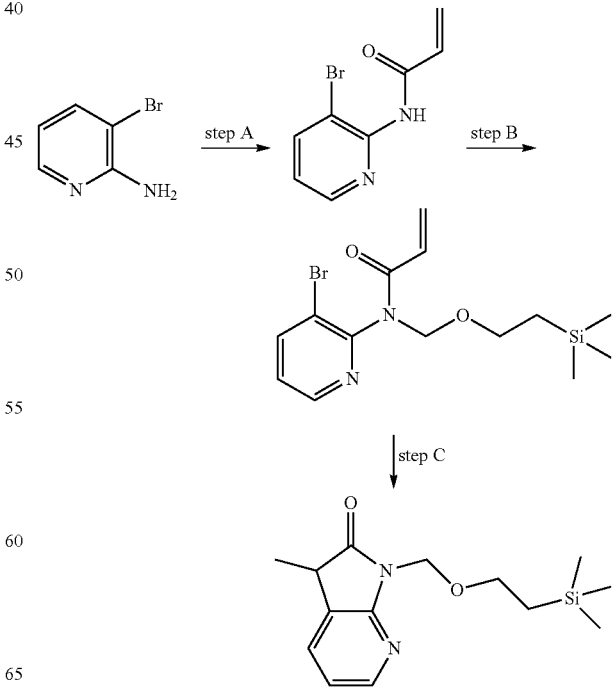

In Scheme 1, step A, about 1 equivalent of 3-bromopyridin-2-amine is treated slowly with a slight excess of acryloyl chloride at low temperature in the presence of about 1.05 equivalents of an organic, non-nucleophilic base, such as TEA, in a suitable organic solvent, such as DCM. The reaction mixture is stirred at low temperature for about 2 hr. The reaction is then quenched with a suitable amount of water, gradually warmed to RT, and the product is isolated and purified utilizing standard techniques well known in the art, such as extraction methods followed by solvent evaporation. For example, the reaction mixture is treated with a suitable organic solvent, such as DCM, and saturated aqueous NaHCO$_3$ with mixing. The layers are separated, the aqueous layer is extracted with DCM, the organic layers are combined, dried over anhydrous Na$_2$SO$_4$, filtered, and concentrated under reduced pressure to provide the product of step A, N-(3-bromopyridin-2-yl)prop-2-enamide, suitable for use without additional purification.

In Scheme 1, step B, N-(3-bromopyridin-2-yl)prop-2-enamide, prepared in step A, is suitably protected in the presence of a strong base in a suitable polar organic solvent. For example, about 1 equivalent of N-(3-bromopyridin-2-yl)prop-2-enamide is added drop wise to a suspension of about 1.5 equivalents of a 60% dispersion of NaH in mineral oil in NMP at 0° C. over 45 min. Then a solution of about 1.5 equivalents of 2-[(trimethylsilyl)ethoxy]methyl chloride in NMP is added slowly at 0-5° C., stirred for about 4 hr, and warmed to about 10° C. The reaction is then quenched with saturated aqueous NH$_4$Cl, and the product is isolated and purified utilizing standard techniques well known in the art, such as extraction methods followed by chromatography. For example, the reaction mixture is treated with a suitable organic solvent, such as MTBE, and the layers are separated; the aqueous layer is extracted with MTBE, the organic layers are combined, dried over anhydrous Na$_2$SO$_4$, filtered, and concentrated under reduced pressure to provide the crude product of step B. The crude product can then be purified by flash chromatography on silica, eluting with a suitable organic solvent mixture, such as hexanes/ethyl acetate, to provide N-(3-bromopyridin-2-yl)-N-{[2-(trimethylsilyl)ethoxy]methyl}prop-2-enamide of step B.

In Scheme 1, step C, about 1 equivalent of N-(3-bromopyridin-2-yl)-N-{[2-(trimethylsilyl)ethoxy]methyl}prop-2-enamide of step B is treated with about 0.1 equivalents of 2,2'-diazene-1,2-diylbis(2-methylpropanenitrile and about 1.1 equivalents of tri-n-butyltin hydride under an atmosphere of nitrogen, in a suitable nonpolar solvent such as toluene. The reaction is then heated in a sealed container at about 85° C. for about 16 hr. The reaction is then gradually cooled to RT and the product is isolated and purified utilizing standard techniques well known in the art, such as solvent removal methods followed by chromatography. For example, the reaction mixture is evaporated under reduced pressure to provide the crude product of step C. The crude product can then be purified by flash chromatography on silica, eluting with a suitable organic solvent mixture, such as hexanes/ethyl acetate, to provide purified 3-methyl-1-{[2-(trimethylsilyl)ethoxy]methyl}-1,3-dihydro-2H-pyrrolo[2,3-b]pyridin-2-one of step C.

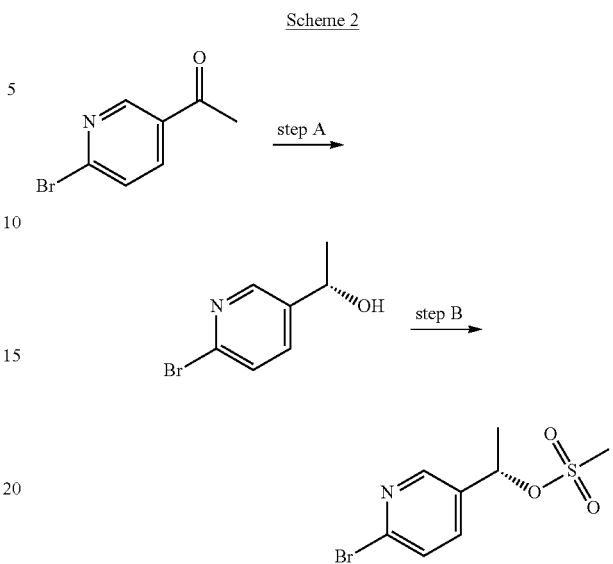

Scheme 2

In Scheme 2, step A, 1-(6-bromopyridin-3-yl)ethanone may be reduced stereoselectively by hydrogenation in the presence of an array of transition metal catalysts. For example, about 1 equivalent 1-(6-bromopyridin-3-yl)ethanone in a suitable polar solvent, such as EtOH:2-propanol (about 1.2 mL:1 mL) is treated with about 0.00075 equivalents chloro {(R)-(+)-2,2'-bis[di(3,5-xylyl)phosphino]-1,1'-binaphthyl}[(2R)-(−)-1-(4-methoxyphenyl)-1-(4-methoxyphenyl-kC)-3-methyl-1,2-butanediamine]ruthenium(II) [(R)-RUCY™-XylBINAP] and about 0.0075 equivalents KO$^t$Bu in an appropriately sealed and evacuated hydrogenation vessel. The system is then filled with hydrogen and stirred at about RT for about 6 hr. The crude product is isolated and purified utilizing standard techniques well known in the art, such as filtration, solvent removal and chromatography. For example, the reaction mixture is filtered, evaporated under reduced pressure to provide the crude product of step C. The crude product can then be purified by flash chromatography on silica, eluting with a suitable organic solvent mixture, such as DCM/MTBE, to provide (1S)-1-(6-bromopyridin-3-yl)ethanol of step A.

In Scheme 2, step B, the product (1S)-1-(6-bromopyridin-3-yl)ethanol of step A is dissolved in a suitable organic solvent such as DCM and treated with about 1.3 equivalents of a suitable organic, non-nucleophilic base such as TEA at about 0° C. About 1.2 equivalents of a suitable sulfonylating reagent, such as methanesulfonyl chloride, are added, and the product is isolated and purified utilizing standard techniques well known in the art, such as extraction. For example, the reaction mixture is treated with water, and the layers are separated; the aqueous layer is extracted twice with DCM, the organic layers are combined, washed with saturated aqueous NaHCO$_3$, dried over anhydrous Na$_2$SO$_4$, filtered, and concentrated under reduced pressure to provide (1S)-1-(6-bromopyridin-3-yl)ethyl methanesulfonate of step B, which can be used in the next step without additional purification.

Scheme 3

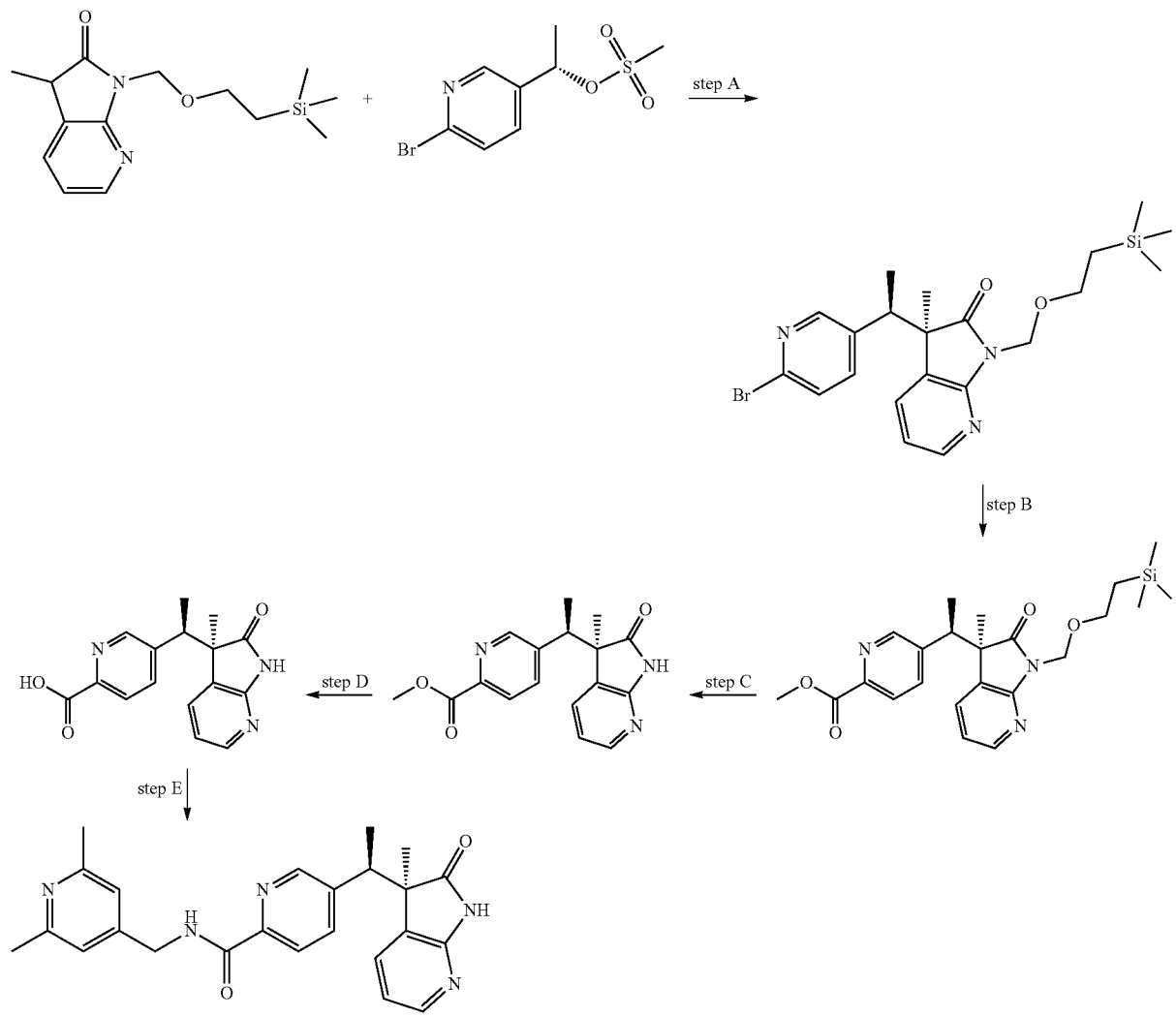

In Scheme 3, step A, about 1.1 equivalents of 3-methyl-1-{[2-(trimethylsilyl)ethoxy]methyl}-1,3-dihydro-2H-pyrrolo[2,3-b]pyridin-2-one, product of Scheme 1, step C, and about 1 equivalent of (1S)-1-(6-bromopyridin-3-yl)ethyl methanesulfonate, product of Scheme 2, step B, are dissolved in a suitable polar organic solvent, such as DMF. The reaction is treated with about 1.2 equivalents of a suitable inorganic base, such as $Cs_2CO_3$ at 0° C. The reaction mixture is gradually warmed to RT and stirred for about 16 hr. The product is isolated and purified utilizing standard techniques well known in the art, such as extraction methods followed by flash chromatography. For example, the reaction mixture is treated with a suitable organic solvent, such as EtOAc, and saturated aqueous $NaHCO_3$ with mixing. The layers are separated, the aqueous layer is extracted again with EtOAc, the organic layers are combined, dried over anhydrous $Na_2SO_4$, filtered, and concentrated under reduced pressure. The crude mixture of diastereomers is purified by flash chromatography on silica gel eluting with a suitable organic solvent mixture, such as hexanes/EtOAc followed by solvent evaporation to provide the purified product of step A, (3R)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one, as the major diastereomer.

In Scheme 3, step B, about 1 equivalent of (3R)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one, the product of step A, is combined in a suitable anhydrous organic solvent mixture such as ACN:MeOH (3:2) containing about 0.1 equivalents of a suitable transition metal catalyst such as palladium(II) acetate, about 0.12 equivalents of a suitable ligand such as 1,1'-bis(diphenylphosphino)ferrocene, and about 2.6 equivalents of a suitable non-nucleophilic organic base such as TEA in a suitable pressure vessel. The reaction is sealed, purged and pressurized with carbon monoxide, and heated to about 100° C. for about 3 hr. The reaction mixture is then allowed to cool to RT and the product is isolated and purified utilizing standard techniques well known in the art, such as filtration, solvent evaporation and flash chromatography. For example, the reaction is filtered, the filtrate is evaporated and the crude product is purified by flash chromatography on silica gel with a suitable eluent, such as hexanes/EtOAc gradient, to provide the purified product of step B, methyl 5-{(1R)-1-

[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylate.

In Scheme 3, step C, about 1 equivalent of the product of step B, methyl 5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylate, is dissolved in a suitable organic solvent such as DCM, and treated with about 20 equivalents of a strong organic acid such as TFA. The reaction is stirred at RT for about 19 hr, and evaporated under reduced pressure. The residue is treated with a suitable organic solvent, such as DCM, and saturated aqueous NaHCO$_3$ with mixing. The layers are separated and the aqueous layer is extracted twice with DCM. The combined organic extracts are dried over Na$_2$SO$_4$, filtered, and concentrated under reduced pressure. The residue is dissolved in a suitable organic solvent such as MeOH and a suitable base such as 1.5 equivalents ethylenediamine is added. The reaction is stirred for about 30 min at RT, evaporated under reduced pressure, and the product is isolated and purified utilizing standard techniques well known in the art, such as extraction methods and chromatography. For example, the reaction residue is evaporated under reduced pressure and diluted with MeOH and a suitable base such as ethylenediamine. The resulting mixture is stirred for about 30 min at RT, and evaporated under reduced pressure. The residue is treated with a suitable organic solvent, such as DCM, and saturated aqueous NaHCO$_3$ with mixing. The layers are separated and the aqueous layer is extracted twice with DCM. The combined organic extracts are dried over Na$_2$SO$_4$, filtered, and concentrated under reduced pressure to give the crude product of step C. The crude product can then be purified by flash chromatography over silica gel, eluting with a suitable organic eluent such as a DCM/EtOAc gradient, to provide the purified product of step C, methyl 5-{(1R)-1-[(3R)-3-methyl-2-oxo-2,3-dihydro-1H-pyrrolo[2,3-b]pyridin-3-yl]ethyl}pyridine-2-carboxylate.

In Scheme 3, step D, about 3 equivalents of a suitable inorganic base, such as LiOH, is added to about 1 equivalent of the product of step C, methyl 5-{(1R)-1-[(3R)-3-methyl-2-oxo-2,3-dihydro-1H-pyrrolo[2,3-b]pyridin-3-yl]ethyl}pyridine-2-carboxylate, in a suitable solvent mixture such as THF/water (5:1). The reaction mixture is stirred at RT for about 2 hr and partitioned between a suitable organic solvent and aqueous acid, such as DCM and 1 M HCl. The mixture is then basified to pH ~2 with saturated aqueous NaHCO$_3$ and extracted about five times with a suitable organic solvent mixture, such as CHCl$_3$/2-propanol (3:1). The combined organic extracts are dried over Na$_2$SO$_4$, filtered, and concentrated under reduced pressure to provide the product of step D, 5-{(1R)-1-[(3R)-3-methyl-2-oxo-2,3-dihydro-1H-pyrrolo[2,3-b]pyridin-3-yl]ethyl} pyridine-2-carboxylic acid, which can be used in the next step without purification.

In Scheme 3, step E, the product of step D, 5-{(1R)-1-[(3R)-3-methyl-2-oxo-2,3-dihydro-1H-pyrrolo[2,3-b]pyridin-3-yl]ethyl} pyridine-2-carboxylic acid may be coupled with a variety of amines or amine hydrochlorides utilizing standard amidation synthetic methods well known in the art. For example, about 1 equivalent of the product of step E can be combined with about 1.7 equivalents of 1-(2,6-dimethylpyridin-4-yl)methamine dihydrochloride, 1.7 equivalents 2,4,6-tripropyl-1,3,5,2,4,6-trioxatriphosphorinane-2,4,6-trioxide and 5 equivalents of TEA in a suitable solvent such as DMF. The reaction mixture is stirred at RT for about 17 hr, and the product can then be isolated and purified utilizing techniques well known in the art, such as extraction and chromatography. For example, saturated aqueous NaHCO$_3$ is added to the reaction mixture which is then extracted with a suitable organic solvent such as DCM. The combined organic extracts are dried over Na$_2$SO$_4$, filtered, and concentrated under reduced pressure to provide the crude product of step E. The crude product can then be purified by flash chromatography on silica gel with a suitable eluent, such as DCM/MeOH gradient, to provide the purified product of step E, N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide.

Scheme 4

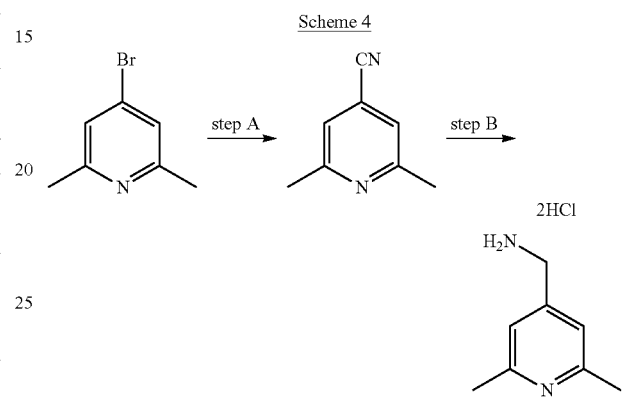

In Scheme 4, step A, about 1.0-1.2 equivalents to Zn(CN)$_2$ may be added to a solution of 4-bromo-2,6-dimethylpyridine in a suitable polar organic solvent such as DMF containing about 5-10 mol % of a suitable transition-metal catalyst/ligand complex, such as tetrakis(triphenylphosphine)palladium (0). After heating for about 5-18 hr, the reaction mixture may be cooled to RT, and the product may be isolated and purified utilizing standard techniques well known in the art, such as extraction methods followed by solvent evaporation or by chromatography. For example, the reaction mixture is treated with a suitable organic solvent, such as EtOAc, and aqueous NH$_4$OH with mixing. The layers are separated, the aqueous layer is extracted with EtOAc, the organic layers are combined, dried over anhydrous Na$_2$SO$_4$, filtered, and concentrated under reduced pressure to provide the crude product of step A. The crude product can then be purified by flash chromatography on silica, eluting with a suitable organic solvent mixture, such as hexanes/ethyl acetate, to provide the product, 4-cyano-2,6-dimethylpyridine, of step A. Alternately, the crude reaction mixture is diluted with a suitable organic solvent, such as MTBE, followed by a basic (pH ~10) aqueous solution, such as 30% NH$_4$OH, the layers are separated, the aqueous phase is additionally extracted with MTBE, and the combined organic extracts are washed with 10% NH$_4$OH, dried over anhydrous Na$_2$SO$_4$, filtered, and concentrated under reduced pressure to provide the product of step A, 4-cyano-2,6-dimethylpyridine, suitable for use without additional purification.

In Scheme 4, step B, the product 4-cyano-2,6-dimethylpyridine of step A may be reduced under a variety of methods well known in the art, such as chemical hydride reduction with a reducing agent such as LiBH$_4$ or NaBH$_4$ or by hydrogenation with a transition-metal such as Pd(OH)$_2$ or Pd on carbon. Additionally, hydrogenation may be performed in the presence of a mineral acid in water or in a suitable organic solvent, such as THF or DMF, to provide the reduced product as the HCl salt. For example, 4-cyano-2,6-dimethylpyridine, product of step A, is dissolved in a suitable organic solvent such as MeOH or EtOH, in the presence of excess HCl either in water or in 1,4-dioxane, and the solution is treated with 5-10% Pd/C. The reaction mixture is subjected to hydrogenation under pressure at about 60 psi at RT overnight. The mixture is filtered, and the filtrate is concentrated to give the crude product of step B. Subsequent precipitation of the product of step B may be achieved by methods well known to those skilled in the art, such as trituration, crystallization, or recrystallization. For example, the crude product of step B may be treated with a mixture of boiling EtOH/EtOAc until dissolution; subsequent cooling with crystallization and collection of the product by filtration may give the product 1-(2,6-dimethyl-pyridin-4-yl)methamine dihydrochloride of Step B. Alternately, the crude product may be suspended in a mixture of MeOH/MTBE, with collection of the resulting solid, 1-(2,6-dimethylpyridin-4-yl)methamine dihydrochloride, product of step B, by filtration.

product is isolated and purified utilizing standard techniques well known in the art, such as extraction methods. For example, the reaction mixture is treated with a suitable organic solvent, such as MTBE, and water, with mixing. The layers are separated, the aqueous layer is extracted again with MTBE, the organic layers are combined, dried over anhydrous $Na_2SO_4$, filtered, and concentrated under reduced pressure to provide the crude product of step A, (3R)-3-[(1R)-1-(6-bromo-3-pyridyl)ethyl]-3-methyl-1H-pyrrolo[2,3-b]pyridin-2-one and (3S)-3-[(1R)-1-(6-bromo-3-pyridyl)ethyl]-3-methyl-1H-pyrrolo[2,3-b]pyridin-2-one, as a mixture of diastereomers.

In Scheme 5, step B, a person skilled in the art may recognize that it may be possible to resolve the diastereomeric products of step A by chiral chromatography or by preparing a chiral salt, such as with the enantiopure mandelic acid, tartaric acid, or camphorsulfonic acid, among other possibilities well known in the art. More specifically, the diastereomeric mixture of (3R)-3-[(1R)-1-(6-bromo-3-pyridyl)ethyl]-3-methyl-H-pyrrolo[2,3-b]pyridin-2-one and

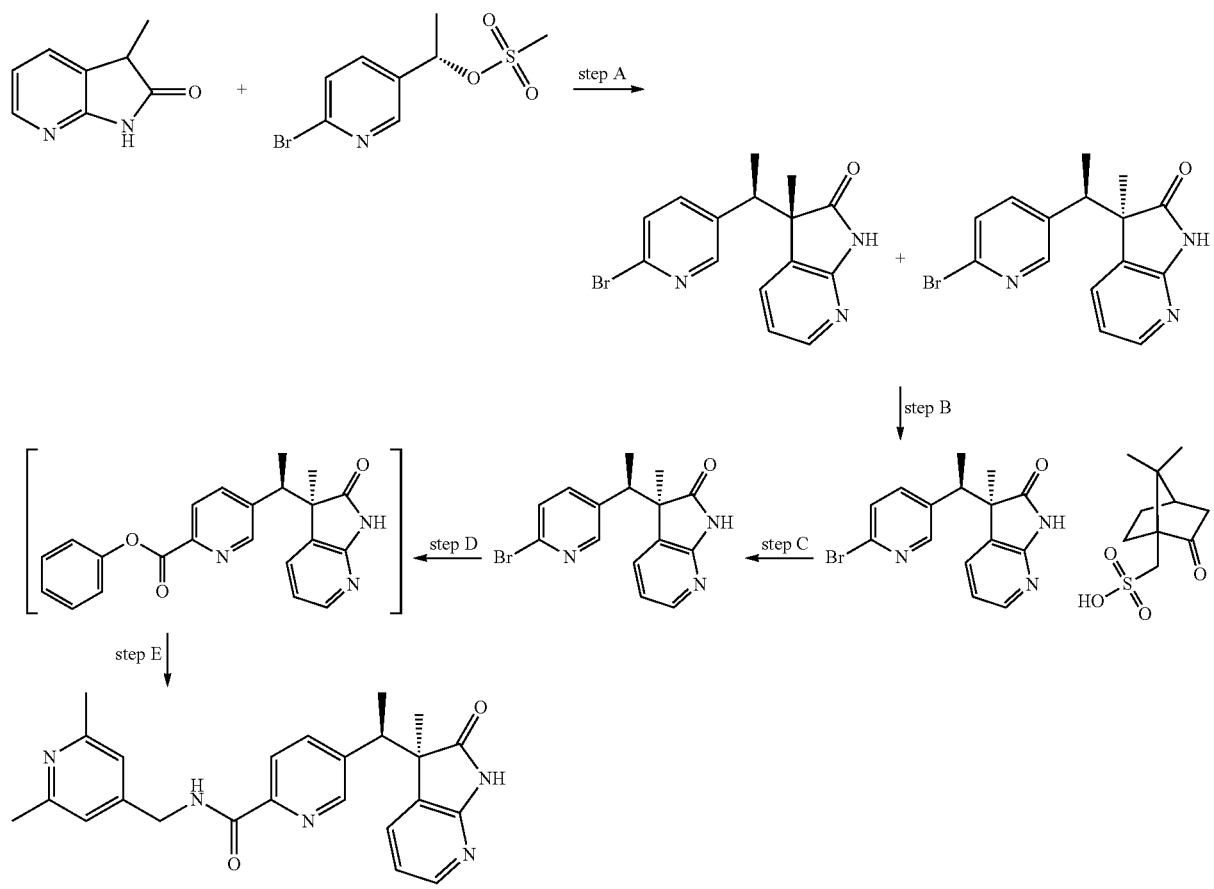

Scheme 5

In Scheme 5, step A, about 1 equivalent of 3-methyl-1,3-dihydropyrrolo[2,3-b]pyridin-2-one and about 1.05 equivalents of (1S)-1-(6-bromopyridin-3-yl)ethyl methanesulfonate, product of Scheme 2, step B, are dissolved in a suitable polar organic solvent, such as DMF. The reaction is treated with about 1-1.2 equivalents of a suitable inorganic base, such as $Cs_2CO_3$ at 0° C. The reaction mixture is gradually warmed to RT and stirred for about 16-48 hr. The (3S)-3-[(1R)-1-(6-bromo-3-pyridyl)ethyl]-3-methyl-1H-pyrrolo[2,3-b]pyridin-2-one, product from step A, may be dissolved in a suitable organic solvent such as EtOAc, and treated with 1-1.5 equivalents of (1S)-(+)-10-camphorsulfonic acid. The reaction mixture may be heated for about 30 min and cooled with stirring to RT overnight, with the resulting precipitate collected by methods well known in the art, such as by vacuum filtration, to give the product (3R)-

3-[(1R)-1-(6-bromo-3-pyridyl)ethyl]-3-methyl-1H-pyrrolo[2,3-b]pyridin-2-one, (1S)-(+)-10-camphorsulfonic acid salt of step B, in high diastereomeric purity.

In Scheme 5, step C, the product from step B, (3R)-3-[(1R)-1-(6-bromo-3-pyridyl)ethyl]-3-methyl-1H-pyrrolo[2,3-b]pyridin-2-one, (1S)-(+)-10-camphorsulfonic acid salt, may be isolated as the free base under conditions well known in the art, such as extraction from an aqueous basic solution and the free base may be crystallized from an appropriate organic solvent. Specifically, (3R)-3-[(1R)-1-(6-bromo-3-pyridyl)ethyl]-3-methyl-1H-pyrrolo[2,3-b]pyridin-2-one, (1S)-(+)-10-camphorsulfonic acid salt is dissolved in aqueous $NaHCO_3$ and extracted several times with an appropriate organic solvent such as EtOAc. The combined organic extracts are washed with saturated aqueous NaCl, dried over $Na_2SO_4$, filtered, and the filtrate is evaporated under reduced pressure to obtain the free base as a residue which is crystallized from MeOH and collected by filtration to obtain the product of step C, (3R)-3-[(1R)-1-(6-bromo-3-pyridyl)ethyl]-3-methyl-1H-pyrrolo[2,3-b]pyridin-2-one.

In Scheme 5, steps D and E, (3R)-3-[(1R)-1-(6-bromo-3-pyridyl)ethyl]-3-methyl-1H-pyrrolo[2,3-b]pyridin-2-one, the product of step C, may be carbonylated utilizing transition-metal catalysis in a suitable organic solvent under conditions well described in the art, with optional isolation of the carbonylated product (step D), followed by direct amidation with an amine to provide the amide product of step E amidation conditions well known in the art. More specifically, the product of step C, (3R)-3-[(1R)-1-(6-bromo-3-pyridyl)ethyl]-3-methyl-1H-pyrrolo[2,3-b]pyridin-2-one, is dissolved in toluene containing about 1.1 equivalents of phenol, about 0.01 equivalents $Pd(OAc)_2$, about 0.01 equivalents 4,5-bis(diphenylphosphino)-9,9-dimethylxanthene, and about 5 equivalents TEA in a sealed reaction vessel pressurized under an atmosphere of CO at 60 psi. The reaction mixture is heated at about 85° C. overnight, cooled slightly, and about 1.1 equivalents of 1-(2,6-dimethylpyridin-4-yl)methamine dihydrochloride is added to the reaction mixture containing unisolated phenyl 5-[(1R)-1-[(3R)-3-methyl-2-oxo-1H-pyrrolo[2,3-b]pyridin-3-yl]ethyl]pyridine-2-carboxylate, product of step D. The reaction mixture is resealed and heated to about 120° C. for about 1 hr. The product of step E may be isolated and purified utilizing standard techniques well known in the art, such as filtration methods followed by chromatography. Specifically, the reaction mixture is cooled, diluted with a suitable organic solvent such as EtOAc, filtered over a bed of diatomaceous earth, and the filtrate is concentrated under reduced pressure to provide the crude product of step E. The crude product is then purified by flash chromatography on silica gel with a suitable eluent, such as a mixture of acetone in hexanes, to obtain the purified product of step E, N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide.

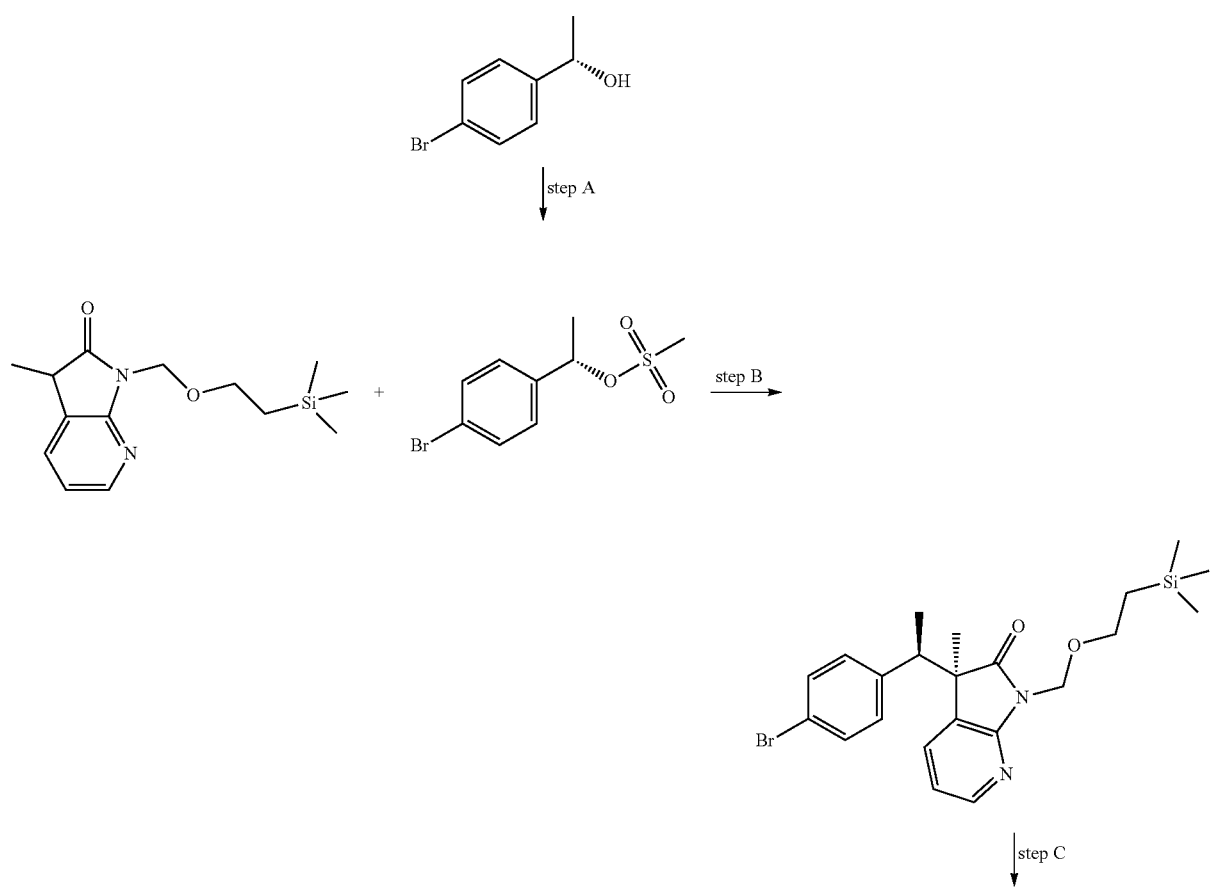

Scheme 6

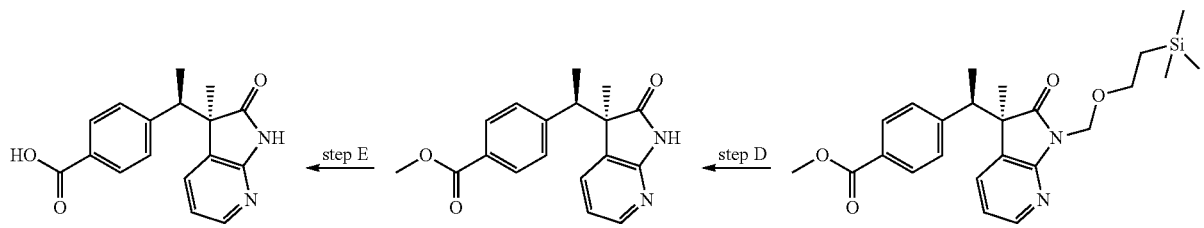

In scheme 6, steps A-E, variously substituted {4-[(1R)-1-[(3R)-3-methyl-2-oxo-1H-pyrrolo[2,3-b]pyridin-3-yl]ethyl]benzoyl}amides may be prepared by analogous methods to those described in Scheme 3. The requisite [(1S)-1-(4-bromophenyl)ethyl]methanesulfonate, product of Scheme 6, step A, may be prepared from (1S)-1-(4-bromophenyl)ethanol (Accel Pharmtech) under analogous conditions to those described in Scheme 2, step B. Treatment of this mesylate with 3-methyl-1-{[2-(trimethylsilyl)ethoxy]methyl}-1,3-dihydro-2H-pyrrolo[2,3-b]pyridin-2-one, product of Scheme 1, step C, under analagous conditions to those described in Scheme 3, step A, may provide (3R)-3-[(1R)-1-(4-bromophenyl)ethyl]-3-methyl-1-(2-trimethylsilylethoxymethyl)pyrrolo[2,3-b]pyridin-2-one, product of Scheme 6, step B. In Scheme 6, step C, the (3R)-3-[(1R)-1-(4-bromophenyl)ethyl]-3-methyl-1-(2-trimethylsilylethoxymethyl)pyrrolo[2,3-b]pyridin-2-one may be carbonylated under similar conditions described in Scheme 3, step B, to provide methyl 4-{(1R)-1-[(3R)-3-methyl-2-oxo-1-(2-trimethylsilylethoxymethyl)pyrrolo[2,3-b]pyridin-3-yl]ethyl}benzoate, and subsequent deprotection of the lactam nitrogen may be accomplished by analogous methods depicted in Scheme 3, step C, to obtain methyl 4-[(1R)-1-[(3R)-3-methyl-2-oxo-1H-pyrrolo[2,3-b]pyridin-3-yl]ethyl]benzoic acid, the product of Scheme 6, step D. Subsequent saponification in Scheme 6, step E, under similar conditions to those depicted in Scheme 3, step D, may give 4-{(1R)-1-[(3R)-3-methyl-2-oxo-1H-pyrrolo[2,3-b]pyridin-3-yl]ethyl}benzoic acid.

Scheme 7

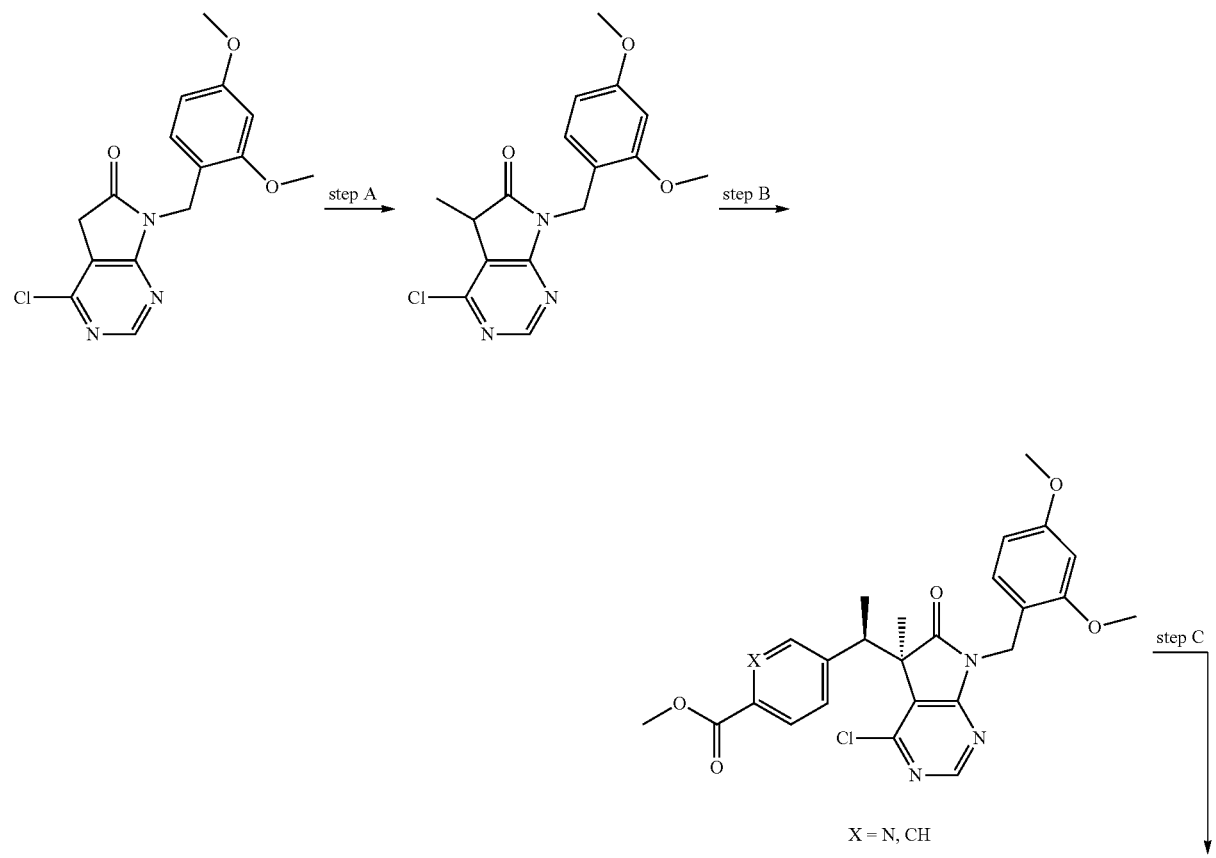

X = N, CH

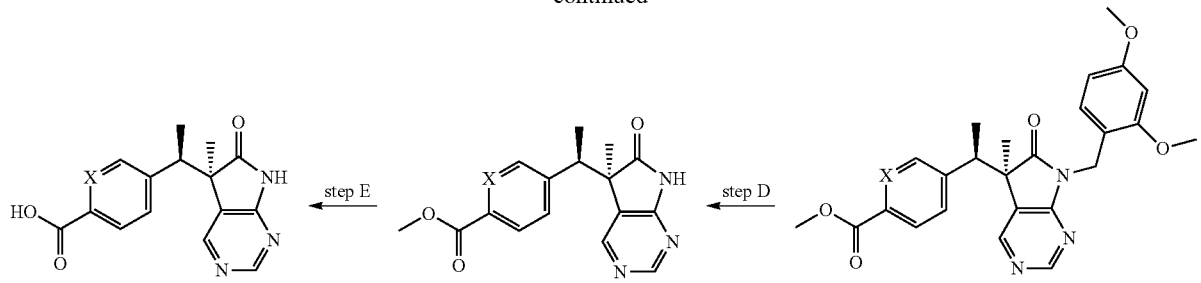

In Scheme 7, step A, 4-chloro-7-(2,4-dimethoxybenzyl)-5,7-dihydro-6H-pyrrolo[2,3-d]pyrimidin-6-one (US 2010/0120801) may be alkylated under basic conditions utilizing a wide variety of conditions well described in the art. For example, about 1 equivalent of 4-chloro-7-(2,4-dimethoxybenzyl)-5,7-dihydro-6H-pyrrolo[2,3-d]pyrimidin-6-one may be dissolved in a suitable polar organic solvent such as DMF and slowly treated with an appropriate strong inorganic base, such as 1 equivalent of NaH, followed by treatment with an appropriate alkyl halide, such as 1 equivalent of $CH_3I$. The reaction mixture is stirred for about 30 min. The product is isolated and purified utilizing standard techniques well known in the art, such as extraction and chromatography methods. For example, the reaction mixture is diluted with saturated aqueous $NH_4Cl$ and extracted with EtOAc. The layers are separated, the organic layer is separated, dried over $Na_2SO_4$, filtered, and concentrated under reduced pressure. The resulting residue is purified by flash chromatography on silica gel eluting with a suitable organic solvent mixture, such as hexanes/EtOAc, followed by solvent evaporation to obtain 4-chloro-7-(2,4-dimethoxybenzyl)-5-methyl-5,7-dihydro-6H-pyrrolo[2,3-d]pyrimidin-6-one, the product of Scheme 7, step A. 4-Chloro-7-(2,4-dimethoxybenzyl)-5-methyl-5,7-dihydro-6H-pyrrolo[2,3-d]pyrimidin-6-one, the product of Scheme 7, step A, may be alkylated with the desired α-methylpyridyl- or α-methylphenyl-mesylate under conditions similar to those described in Scheme 3, step A or Scheme 6, step B, respectively, to provide the product of Scheme 7, step B (X=N, CH). The product of Scheme 7, step B (X=N, CH) may be dechlorinated under hydrogenation conditions well appreciated in the art. For example, the product of Scheme 7, step B (X=N, CH) is dissolved in a suitable polar organic solvent such as MeOH, treated with an appropriate transition metal catalyst suitable for hydrogenation, such as 5% Pd on carbon, and subjected to hydrogenation under conditions well known in the art, for example, under an atmosphere of hydrogen at a pressure of 20-60 psi. The reaction mixture is filtered and the filtrate is evaporated under reduced pressure. The crude dechlorinated product may be used as is (X=N) or may be purified (X=CH) utilizing standard techniques well known in the art, such as extraction and chromatography methods, For example, the crude filtrate is diluted with saturated aqueous $NaHCO_3$, extracted with an appropriate organic solvent such as DCM, and the layers separated. The organic extracts are dried over $Na_2SO_4$, concentrated under reduced pressure, and the resulting residue is purified by flash chromatography on silica gel, eluting with a suitable organic solvent mixture, such as hexanes/EtOAc, to obtain the dechlorinated product of Scheme 7, step C (X=CH) after solvent evaporation. The lactam nitrogen of the product of Scheme 7, step C may be unmasked by conditions well appreciated in the art. For example, about 1 equivalent of the product of Scheme 7, step C is dissolved in a mixture of an appropriate high-boiling organic solvent, such as anisole, and a strong organic acid, such as TFA. The reaction mixture is heated under either thermal or microwave conditions for about 2-18 hr, and the crude product is obtained by extraction methods such as diluting the reaction mixture with a mixture of saturated aqueous $NaHCO_3$ and an appropriate organic solvent such as DCM. The layers are separated, the organic layer is dried over $Na_2SO_4$ and filtered, and the crude product is purified by flash chromatography on silica gel, eluting with a suitable organic solvent mixture, such as DCM/EtOAc/MeOH (X=N) or DCM/EtOAc (X=CH), to obtain the product of Scheme 7, step D; saponification under conditions similar to those described in Scheme 3, step D (X=N) or Scheme 6, step E (X=CH), yields the desired acid product of Scheme 7, step E.

Scheme 8

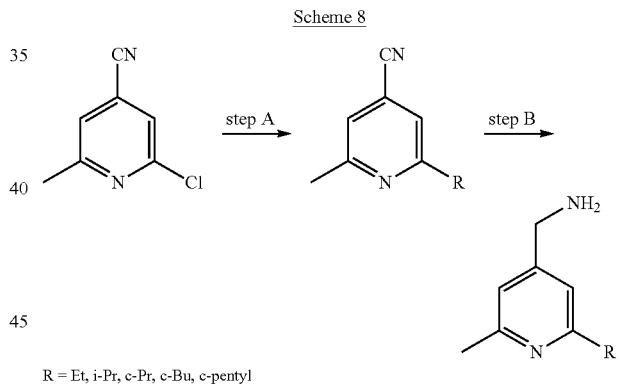

R = Et, i-Pr, c-Pr, c-Bu, c-pentyl

Scheme 8 depicts the preparation of 2-substituted-6-methyl-pyridylmethanamines. In Scheme 8, step A, a person of ordinary skill in the art may appreciate the conversion of a 2-chloropyridine to a 2-alkylpyridine using Grignard, alkyllithium, alkylboronate or alkylzinc reagent. For example, treatment of about 3.0-3.6 equivalents 2-chloro-6-methylisonicotinonitrile (Bioorganic & Medicinal Chemistry Letters, 20(2), 576-580; 2010) with about 1.0-1.5 equivalents of an appropriately substituted Grignard, alkylboronate or alkylzinc reagent in a suitable polar solvent, such as NMP or 1,4-dioxane, or in a biphasic mixture of a suitable organic solvent such as toluene, benzene, or DMF containing water, in the presence of about 0.1-0.2 equivalents of a transition metal catalyst, for example iron (III) acetoacetate (R=Et), $Pd(OAc)_2$ in the presence of a suitable phosphine ligand such as tricyclohexylphosphine tetrafluoroborate, or [1,1'-bis(diphenylphosphino)-ferrocene]dichloropalladium(II) (R=i-Pr, c-Pr, c-Bu, c-pentyl) from about room temperature to about 120° C., gives the crude 2-alkyl product of Scheme 8, step A, which may be isolated and purified under conditions well known in the art, such as extraction and chromatography. For example, the reaction is diluted with water and filtered over a bed of diatomaceous earth, and the filtrate is extracted with an appropriate organic solvent such as EtOAc or DCM. The organic extract is dried over Na$_2$SO$_4$, filtered, concentrated under reduced pressure, and purified by flash chromatography on silica gel using hexanes or heptanes/EtOAc, to obtain the desired 2-alkyl-6-methyl-4-pyridinecarbonitrile, product of Scheme 8, step A. The carbonitrile moiety may be reduced to the methylamine under an array of conditions well appreciated in the art. For example, the desired 2-alkyl-6-methyl-4-pyridinecarbonitrile, about 1 equivalent of the product of Scheme 8, step A, may be treated with excess Raney nickel under an atmosphere of hydrogen at 20-60 psi in a suitable polar solvent mixture, such as NH$_3$ in MeOH. The reaction mixture may be filtered, concentrated, and the resulting residue triturated sequentially with an appropriate mixture of organic solvents, such as toluene, ACN, MeOH/toluene, and ACN/toluene, with subsequent filtration, to obtain the appropriately substituted (2-alkyl-6-methyl-4-pyridyl)methanamine as the dihydrochloride salt. Alternatively, the resulting crude product may be isolated and purified under conditions well known in the art, such as extraction and chromatography methods, to obtain the appropriately substituted (2-alkyl-6-methyl-4-pyridyl)methanamine as the free base.

Scheme 9

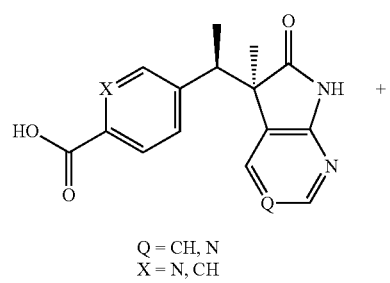

Q = CH, N
X = N, CH

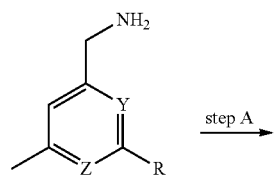

R = Et, i-Pr, c-Pr, c-Bu, c-pentyl, CN
Y = CH, N
Z = N, CH

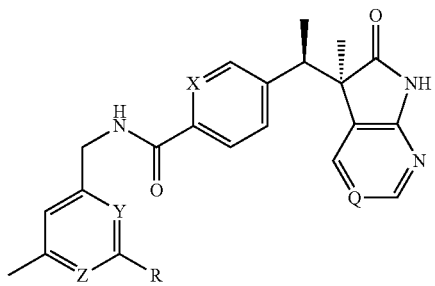

Formula IV

Scheme 9 depicts the preparation of compounds of Formula IV wherein the appropriate carboxylic acid may be coupled to an appropriate amine under an array of amide coupling conditions well known in the art. For example, the amide coupling reaction may be performed analogously to that depicted in Scheme 3, step E, or may be performed with such coupling agents as EDCI, HOBt, HOAT, HATU, or T3P, among many others well described in the literature.

Scheme 10

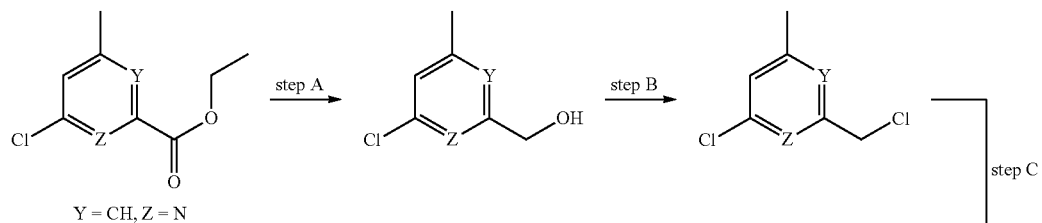

Y = CH, Z = N
Y = N, Z = CH

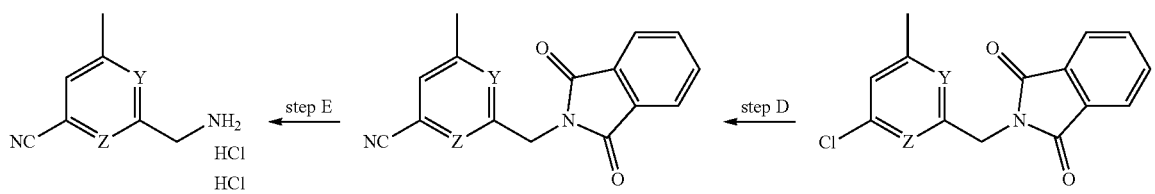

Scheme 10 depicts the preparation of 6-(aminomethyl)-4-methyl-pyridine-2-carbonitrile dihydrochloride. In Scheme 10, step A, reduction of ethyl 2-pyridine-carboxylates may be accomplished under a wide array of methods well described in the art. For example, about 1 equivalent of ethyl 6-chloro-4-methylpyridine-2-carboxylate (Y=CH, Z=N) is treated with about 1.7 equivalents of sodium borohydride in EtOH at RT to obtain (6-chloro-4-methyl-2-pyridyl)methanol, the product of Scheme 10, step A (Y=CH, Z=N), suitable for use without additional purification. Halogenation to the alkyl halide may be recognized by one of ordinary skill under various halogenation conditions. For example, about 1 equivalent of the product of Scheme 10, step A, (6-chloro-4-methyl-2-pyridyl)methanol (Y=CH, Z=N) is treated with about 2 equivalents of thionyl chloride in a suitable organic solvent such as DCM or $CHCl_3$ from about RT to reflux, and evaporation of the solvents may yield the desired 2-chloro-6-(chloromethyl)-4-methyl-pyridine, the product of Scheme 10, step B (Y=CH, Z=N), suitable for use without additional purification. The product of Scheme 10, step B, 2-chloro-6-(chloromethyl)-4-methyl-pyridine (Y=CH, Z=N), may be treated with a variety of protected amines suitable to withstand additional functionalization. For example, about 1 equivalent of potassium phthalimide may be treated with 2-chloro-6-(chloromethyl)-4-methyl-pyridine, the product of Scheme 10, step B (Y=CH, Z=N), in a suitable polar solvent such as DMF. Subsequent dilution with water may yield the solid product of Scheme 10, step C (Y=CH, Z=N), 2-[(6-chloro-4-methyl-2-pyridyl)methyl]isoindoline-1,3-dione, which may be isolated by methods well known in the art, such as filtration. The chloro moiety of 2-[(6-chloro-4-methyl-2-pyridyl)methyl]isoindoline-1,3-dione, product of Scheme 10, step C (Y=CH, Z=N), may be displaced with a wide of nucleophiles as well described in the literature, such as by SNAR reaction or by transition metal-mediated processes. For example, about 1 equivalent of the product of Scheme 10, step C (Y=CH, Z=N), 2-[(6-chloro-4-methyl-2-pyridyl)methyl]isoindoline-1,3-dione, may be treated with about 0.75 equivalents of zinc cyanide in the presence of about 0.05 equivalents of [1,1'-bis(diphenylphosphino)ferrocene]palladium(II) dichloride and about 0.25 equivalents of elemental zinc in a suitable polar organic solvent such as DMF or DMSO with heating from 100-140° C. A person skilled in the art will recognize that the product of this transformation may be isolated and purified by standard techniques well known in the art, such as extraction and chromatography. For example, the cooled reaction mixture may be diluted with water and extracted with a suitable solvent such as DCM or EtOAc, washed sequentially with $NH_4OH$ and saturated aqueous NaCl, and the organic extract may be dried over $Na_2SO_4$ or $MgSO_4$. The resulting crude product may be subjected to flash chromatography on silica eluting with a suitable organic solvent mixture, such as hexanes/ethyl acetate, to provide the product, 6-[(1,3-dioxoisoindolin-2-yl)methyl]-4-methyl-pyridine-2-carbonitrile, of Scheme 10, step D (Y=CH, Z=N). Removal of the amine protecting group may be accomplished by one of ordinary skill in the art. For example, treatment of about 1 equivalent of 6-[(1,3-dioxoisoindolin-2-yl)methyl]-4-methyl-pyridine-2-carbonitrile, the product of Scheme 10, step D (Y=CH, Z=N), with about 2 equivalents of hydrazine hydrate in a suitable polar organic solvent such as EtOH under reflux, may yield the crude deprotected amine upon solvent evaporation.

Subsequent isolation and purification of the crude amine may be accomplished by standard techniques known in the art, such as selective cation exchange and salt preparation. For example, the crude amine may be passed through an SCX column, eluting with a mixture of $NH_3$/MeOH; the methanolic ammonia fractions may be evaporated, the resulting residue redissolved in MeOH, and the resulting solution treated with 2-10 equivalents of HCl in a suitable organic solvent, such as $Et_2O$ or 1,4-dioxane, to obtain the solid 6-(aminomethyl)-4-methyl-pyridine-2-carbonitrile dihydrochloride after collection by filtration. The syntheses of compounds where Y=N and Z=CH may be performed via analogous methods.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R- or S-configuration of the compound of the invention may be determined by standard techniques such as X-ray analysis and correlation with chiral-HPLC retention time.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.5 m; gradient: 5-100% B in 3 min, then 100% B for 0.75 min, or 5-95% B in 1.5 min, then 95% B for 0.25 min; column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 m; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min or 5-95% B in 1.5 min, then 95% B for 0.25 min; column temperature: 50° C.+/−10° C.; flow rate: 1.2 mL/min; Solvent A: 10 mM $NH_4HCO_3$ pH 9; Solvent B: ACN; wavelength: 214 nm.

Preparative reversed phase chromatography is performed on an AGILENT® 1200 LC-ES/MS equipped with a Mass Selective Detector mass spectrometer and a LEAP® autosampler/fraction collector. High pH methods are run on a 75×30 mm PHENOMENEX® GEMINI®-NX, 5μ particle size column with a 10×20 mm guard. Flow rate of 85 mL/min. Eluent is 10 mM ammonium bicarbonate (pH 10) in acetonitrile.

NMR spectra are performed on a Bruker AVIII HD 400 MHz NMR Spectrometer or a Varian VNMRS 400 MHz NMR Spectrometer, obtained as $CDCl_3$ or $(CD_3)_2SO$ solutions reported in ppm, using residual solvent [$CDCl_3$, 7.26 ppm; $(CD_3)_2SO$, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

X-Ray Powder Diffraction: The XRD patterns of crystalline solids are obtained on a Bruker D4 Endeavor X-ray powder diffractometer, equipped with a CuKa source Preparation 1

N-(3-bromopyridin-2-yl)prop-2-enamide

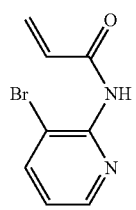

Scheme 1, step A: A solution of 3-bromopyridin-2-amine (100.0 g, 578.0 mmol) and TEA (82 mL, 588.0 mmol) in DCM (2.8 L) is cooled to −78° C. Acryloyl chloride (47.5 mL, 584.0 mmol) in DCM (200 mL) is added drop wise over 2 hr. The reaction mixture is stirred at −75° C. for 2 hr. Water and then saturated aqueous NaHCO$_3$ are added and the layers are separated. The organic layer is dried over Na$_2$SO$_4$, filtered, and concentrated under reduced pressure to give a solid. To the solid is added DCM (200 mL) and MTBE (600 mL) and the mixture is concentrated under reduced pressure to about 300 mL. The resulting off-white solid is filtered and dried under vacuum overnight to give the title compound (97.1 g, 74% yield). LC-ES/MS (m/z for $^{79}$Br/$^{81}$Br): 227.0/229.0 (M+H).

Preparation 2

N-(3-bromopyridin-2-yl)-N-{[2-(trimethylsilyl)ethoxy]methyl}prop-2-enamide

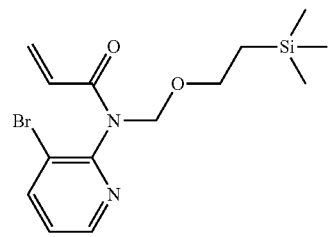 [SMILES: C=CC(=O)N(COCC[Si](C)(C)C)c1ncccc1Br]

Scheme 1, step B: N-(3-bromopyridin-2-yl)prop-2-enamide (42 g, 185.0 mmol) in NMP (800 mL) is added over 45 min to a suspension of NaH (60% in mineral oil, 11.1 g, 277.0 mmol) in NMP (800 mL) at 0° C. and stirred at 0-5° C. for 30 min. 2-[(trimethylsilyl)ethoxy]methyl chloride (50 mL, 280.0 mmol) is added drop wise at 0-5° C. over 30 min. The reaction mixture is stirred at 0° C. for 4 hr and then warmed to 10° C. After 15 min at 10° C., saturated aqueous NH$_4$Cl and water are added and the mixture is extracted with MTBE. The organic layers are combined and washed sequentially water and then saturated aqueous NaCl, dried over Na$_2$SO$_4$, filtered, and concentrated under reduced pressure to give a residue. The residue is purified by flash chromatography over silica, eluting with hexanes/EtOAc (gradient from 1:0 to 3:1) to give the title compound (48.0 g, 73% yield), after solvent evaporation. LC-ES/MS (m/z for $^{79}$Br/$^{81}$Br): 357.0/359.0 (M+H).

Preparation 3

3-methyl-1-{[2-(trimethylsilyl)ethoxy]methyl}-1,3-dihydro-2H-pyrrolo[2,3-b]pyridin-2-one

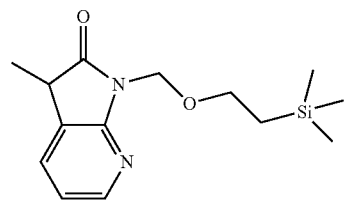

Scheme 1, step C: To a solution of N-(3-bromopyridin-2-yl)-N-{[2-(trimethylsilyl)ethoxy]methyl}prop-2-enamide (2.17 g, 6.1 mmol) in toluene (61 mL) is added 2,2'-diazene-1,2-diylbis(2-methylpropanenitrile) (0.100 g, 0.61 mmol) and tri-n-butyltin hydride (1.94 g, 6.7 mmol). The reaction mixture is purged with nitrogen and heated to 85° C. for 16 hr. The mixture is cooled to RT and concentrated under reduced pressure to give a residue. The residue is purified by flash chromatography over silica, eluting with hexanes/EtOAc (gradient from 1:0 to 1:1) to give the title compound (1.08 g, 64% yield), after solvent evaporation. LC-ES/MS (m/z): 279.0 (M+H).

---

λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

Preparation 4

(1S)-1-(6-bromopyridin-3-yl)ethanol

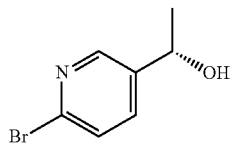

Scheme 2, step A: A solution of chloro{(R)-(+)-2,2'-bis[di(3,5-xylyl)phosphino]-1,1'-binaphthyl}[(2R)-(−)-1-(4-methoxyphenyl)-1-(4-methoxyphenyl-kC)-3-methyl-1,2-butanediamine]ruthenium(II) (103 mg, 0.087 mmol) and KO$^t$Bu (1.0 M in t-BuOH, 0.88 mL, 0.88 mmol) in anhydrous 2-propanol (15 mL) under nitrogen is added to a solution of 1-(6-bromopyridin-3-yl)ethanone (23.5 g, 117.0 mmol) in anhydrous EtOH (100 mL)/anhydrous 2-propanol (85 mL) in a 600 mL Parr autoclave under nitrogen. The autoclave is sealed, evacuated, pressurized to 207 kPa with hydrogen, and stirred at RT for about 6 hr. The reaction mixture is concentrated under reduced pressure to give a solid residue and dried under vacuum overnight. The residue is purified by flash chromatography over silica, eluting with DCM/MTBE (gradient from 9:1 to 3:1) to give the title compound (23.7 g, 94% yield). LC-ES/MS (m/z for $^{79}$Br/$^{81}$Br): 202.0/204.0 (M+H). Chiral HPLC indicates 99.3% ee; $t_R$=6.32 min [254 nm; LC Column: CHIRALCEL® OD-H 4.6×150 mm; 5.0 µL injection; 10% 2-propanol in heptane (containing 0.2% DMEA); Column Temp: 25° C.; Flow Rate: 1.0 mL/min].

Preparation 5

(1S)-1-(6-bromopyridin-3-yl)ethyl methanesulfonate

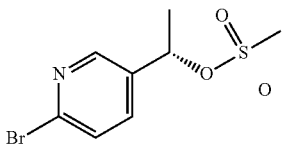

Scheme 2, step B: To a stirred solution of (1S)-1-(6-bromopyridin-3-yl)ethanol (3.00 g, 14.8 mmol) and TEA (2.69 mL, 19.3 mmol) in DCM (30 mL) at 0° C. is added methanesulfonyl chloride (1.38 mL, 17.8 mmol). After 2 hr at 0° C., water and DCM are added and the layers are separated. The aqueous layer is extracted with DCM. The organic layers are combined and washed sequentially with saturated aqueous NaHCO$_3$ and saturated NaCl, dried over Na$_2$SO$_4$; filtered, and concentrated under reduced pressure to give the title compound (4.13 g, 99% yield). LC-ES/MS (m/z for $^{79}$Br/$^{81}$Br): 280.0/282.0 (M+H). $^1$H NMR (CDCl$_3$) δ 1.74 (d, J=6.6 Hz, 3H), 2.93 (s, 3H), 5.76 (q, J=6.6 Hz, 1H), 7.54 (d, J=8.3 Hz, 1H), 7.62 (dd, J=2.5, 8.3 Hz, 1H), 8.41 (d, J=2.5 Hz, 1H).

Preparation 6

(3R)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one (Major diastereomer) and (3S)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one (Minor diastereomer)

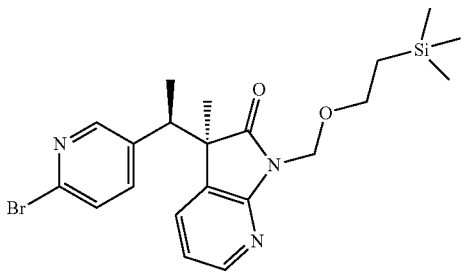

Major diastereomer

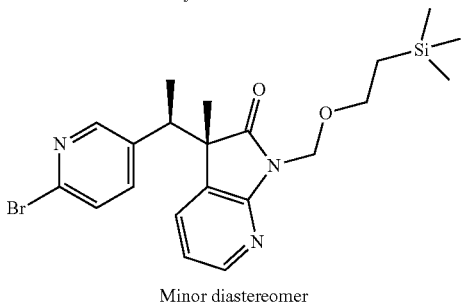

Minor diastereomer

Scheme 3, step A: To a stirred solution of 3-methyl-1-{[2-(trimethylsilyl)ethoxy]methyl}-1,3-dihydro-2H-pyrrolo[2,3-b]pyridin-2-one (4.99 g, 90% purity, 16.1 mmol) and (1S)-1-(6-bromopyridin-3-yl)ethyl methanesulfonate (4.12 g, 14.7 mmol) in DMF (74 mL) under nitrogen at 0° C. is added Cs$_2$CO$_3$ (5.75 g, 17.6 mmol). The reaction mixture is thoroughly purged with nitrogen and gradually warmed to RT. After stirring for 16 hr at RT, EtOAc and saturated aqueous NaHCO$_3$ are added and the layers are separated. The aqueous layer is extracted again with EtOAc, the organic layers are combined, dried over Na$_2$SO$_4$, filtered, and concentrated under reduced pressure to give a red oil. The crude product is purified by flash chromatography over silica, eluting with hexanes/EtOAc (from 9:1 to 3:2) to obtain the title compound (4.61 g, 65% yield) as the major diastereomer, which elutes first, and the minor diastereomer, (3S)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one, which elutes second (0.34 g, 5% yield), after solvent evaporation.

Major diastereomer: LC-ES/MS (m/z for $^{79}$Br/$^{81}$Br): 462.0/464.0 (M+H). $^1$H NMR (CDCl$_3$) δ −0.02 (s, 9H), 0.90-1.03 (m, 2H), 1.20 (d, J=7.2 Hz, 3H), 1.35 (s, 3H), 3.30 (q, J=7.2 Hz, 1H), 3.60-3.64 (m, 2H), 5.19-5.25 (m, 2H), 6.94 (dd, J=5.2, 7.3 Hz, 1H), 7.05 (dd, J=1.6, 7.3 Hz, 1H), 7.33 (dd, J=2.5, 8.2 Hz, 1H), 7.42 (d, J=8.2 Hz, 1H), 8.10 (d, J=2.5 Hz, 1H), 8.21 (dd, J=1.6, 5.2 Hz, 1H).

Minor diastereomer: LC-ES/MS (m/z for $^{79}$Br/$^{81}$Br): 462.0/464.0 (M+H). $^1$H NMR (CDCl$_3$) δ −0.03 (s, 9H), 0.81-0.96 (m, 2H), 1.44 (d, J=7.2 Hz, 3H), 1.47 (s, 3H), 3.30 (q, J=7.2 Hz, 1H), 3.34-3.40 (m, 2H), 4.96-5.02 (m, 2H), 7.03 (dd, J=5.3, 7.3 Hz, 1H), 7.06 (dd, J=2.5, 8.3 Hz, 1H), 7.21 (d, J=8.3 Hz, 1H), 7.61 (dd, J=1.6, 8.2 Hz, 1H), 7.92 (d, J=2.5 Hz, 1H), 8.22 (dd, J=1.6, 5.3 Hz, 1H).

Preparation 7

Methyl 5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylate

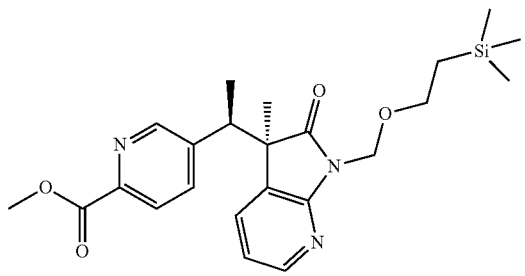

Scheme 3, step B: Palladium(II) acetate (227 mg, 0.961 mmol), 1,1'-bis(diphenylphosphino)ferrocene (670 mg, 1.17 mmol), (3R)-3-[(1R)-1-(6-bromopyridin-3-yl)ethyl]-3-methyl-1-{[2-(trimethylsilyl)ethoxy]methyl}-1,3-dihydro-2H-pyrrolo[2,3-b]pyridin-2-one (4.61 g, 9.58 mmol), anhydrous MeOH (40 mL), anhydrous ACN (60 mL), and TEA (3.5 mL, 25 mmol) are combined in a 300 mL Parr autoclave with a mechanical stirrer. The autoclave is sealed, purged with CO, pressurized to 689 kPa with CO, and heated to 85° C. with stirring. After 3 hr at 100° C., the reaction mixture is cooled to room temperature and filtered. The filtrate is concentrated under reduced pressure to give a solid residue. The residue is suspended in EtOAc (200 mL) and filtered again. The filtrate is concentrated under reduced pressure to give an orange residue. The orange residue is purified by flash chromatography over silica, eluting with hexanes/EtOAc (gradient from 7:3 to 8:2) to give the title compound (3.69 g, 86% yield), after solvent evaporation of the desired fractions. LC-ES/MS (m/z): 442.2 (M+H). The material is analyzed by chiral SFC (Column: Lux Cellulose-4; eluent: 20:80, MeOH:CO$_2$; flow: 5 mL/min at UV 225 nm) indicating 98.3% ee and corresponding to the first eluting isomer with $t_R$=1.33 min.

Preparation 8

Methyl 5-{(1R)-1-[(3R)-3-methyl-2-oxo-2,3-dihydro-1H-pyrrolo[2,3-b]pyridin-3-yl]ethyl}pyridine-2-carboxylate

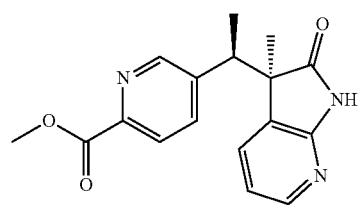 [SMILES: COC(=O)c1ccc([C@@H](C)[C@@]2(C)C(=O)Nc3ncccc32)cn1]

Scheme 3, step C: To a solution of methyl 5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylate (3.67 g, 8.21 mmol) in DCM (27.4 mL) at RT is added TFA (12.4 mL, 164.0 mmol). After 19 hr, the solution is concentrated under reduced pressure to give a residue. The residue is partitioned between DCM and saturated aqueous NaHCO$_3$ and the layers are separated. The aqueous layer is extracted twice with DCM. The organic layers are combined, dried over Na$_2$SO$_4$, filtered, and concentrated under reduced pressure to give a residue. To the residue is added MeOH (109 mL) and ethylenediamine (0.826 mL, 12.3 mmol). After 30 min, the solution is concentrated under reduced pressure to give a residue. DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a residue. The residue is purified by flash chromatography over silica, eluting with DCM/EtOAc (gradient from 1:0 to 0:1) to give the title compound (1.80 g, 70% yield), after solvent evaporation. LC-ES/MS (m/z): 312.0 (M+H).

Preparation 9

5-{(1R)-1-[(3R)-3-methyl-2-oxo-2,3-dihydro-1H-pyrrolo[2,3-b]pyridin-3-yl]ethyl}pyridine-2-carboxylic acid

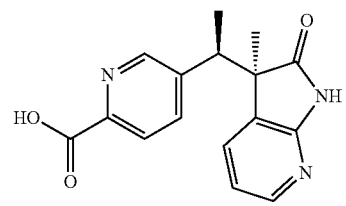 [SMILES: C[C@H](c1ccc(C(=O)O)nc1)[C@@]1(C)C(=O)Nc2ncccc21]

Scheme 3, step D: To a solution of methyl 5-{(1R)-1-[(3R)-3-methyl-2-oxo-2,3-dihydro-1H-pyrrolo[2,3-b]pyridin-3-yl]ethyl}pyridine-2-carboxylate (1.80 g, 5.78 mmol) in THF (28.9 mL) at RT is added a solution of LiOH (415 mg, 17.3 mmol) in water (5.8 mL). After 2 hr, the reaction mixture is diluted with DCM and 1.0 M HCl. NaCl is added until saturation then saturated aqueous NaHCO$_3$ is added slowly at RT until the mixture reaches pH ~2. The layers are separated, and the aqueous layer is extracted five times with CHCl$_3$/2-propanol (3:1). The organic layers are combined, dried over Na$_2$SO$_4$, filtered, and concentrated under reduced pressure to give the title compound (1.71 g, 99% yield). LC-ES/MS (m/z): 298.0 (M+H).

Preparation 10

5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylic acid

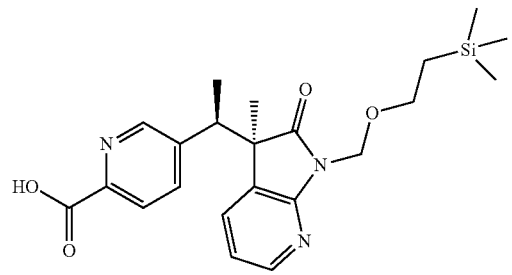 [SMILES: C[C@H](c1ccc(C(=O)O)nc1)[C@@]1(C)C(=O)N(COCC[Si](C)(C)C)c2ncccc21]

To a solution of methyl 5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylate (16.25 g, 36.8 mmol) in MeOH (162 mL) and water (32.5 mL) at RT is added LiOH (2.64 g, 110.0 mmol). The reaction mixture is stirred for 1 hr at RT and 1.0 M HCl (115 mL, 115.0 mmol) is added. The mixture is diluted with EtOAc and water and the layers are separated. The aqueous layer is extracted with EtOAc. The organic layers are combined, dried over Na₂SO₄, filtered, concentrated under reduced pressure, and dried under vacuum to give the title compound (16.2 g, quantitative yield), suitable for use without additional purification. LC-ES/MS (m/z): 428.2 (M+H).

Preparation 11

N-[(2,6-dimethylpyridin-4-yl)methyl]-5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxamide

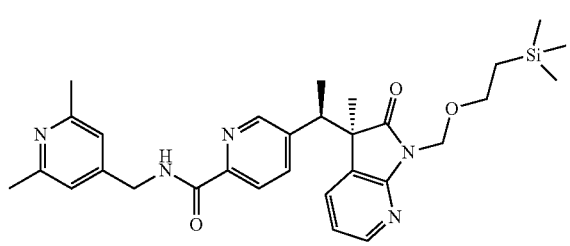

To a stirred solution of 5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxylic acid (16.2 g, 37.9 mmol) and 1-(2,6-dimethylpyridin-4-yl)methanamine dihydrochloride (7.20 g, 41.7 mmol) in DMF (162 mL) at RT is added diisopropylethylamine (39.6 mL, 227.0 mmol) and BOP (19.4 g, 41.7 mmol) in three portions over 10 min. The reaction mixture is stirred for 1.5 hr at RT and 1-(2,6-dimethylpyridin-4-yl)methanamine dihydrochloride (1.4 g, 8.1 mmol) is added. The reaction mixture is stirred for 45 min at RT and BOP (3.6 g, 8.1 mmol) is added. The reaction mixture is stirred for 1 hr at RT and diluted with MTBE and water. The layers are separated and the aqueous layer is extracted with MTBE. The organic layers are combined, washed twice with water, filtered, concentrated under reduced pressure, and dried under vacuum to give the title compound (15 g, 72% yield). LC-ES/MS (m/z): 546.2 (M+H).

Preparation 12

2,6-dimethylpyridine-4-carbonitrile

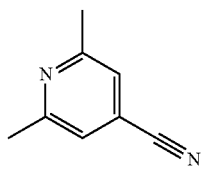

Scheme 4, step A: Zinc cyanide (3.82 g, 31.9 mmol) is added to a mixture of 4-bromo-2,6-dimethylpyridine (5.09 g, 26.5 mmol) and DMF (40 mL) stirring under nitrogen at RT. Nitrogen is bubbled through the stirred suspension for 15 min, and tetrakis(triphenylphoshpine) palladium(0) (1.54 g, 1.33 mmol) is added. After heating the reaction mixture at 120° C. for 5.5 hr, the mixture is cooled to RT and diluted with EtOAc (150 mL). The solids are removed via paper filtration and the filter cake is washed with EtOAc (50 mL). The combined organic filtrate and wash is washed sequentially with 15% aqueous NH₃ (2×50 mL), water (50 mL) and saturated aqueous NaCl, dried over Na₂SO₄, filtered, and concentrated under reduced pressure to give a yellow solid. The crude product is purified by flash chromatography on silica, eluting with hexanes/ethyl acetate (gradient from 9:1 to 1:1). The pure chromatography fractions are combined and concentrated under reduced pressure to give the title compound (2.79 g, 77% yield). ¹H NMR (CDCl₃): δ 2.61 (s, 6H), 7.21 (s, 2H).

Alternative Procedure for Preparation 12

2,6-dimethylpyridine-4-carbonitrile

Scheme 4, step A: 4-Bromo-2,6-dimethylpyridine (235.0 g, 1263.1 mmol) is dissolved in anhydrous DMF (250 mL) in a three-necked round bottom flask equipped with a mechanical stirrer, reflux condenser, and N₂ inlet and N₂ is bubbled through the solution for 20 min. A portion of the solution (~150 mL) is transferred to an addition funnel via a cannula under N₂. Zinc cyanide (150.0 g, 1277.4 mmol) and tetrakis(triphenylphosphine)palladium (0) (15.0 g, 13.0 mmol) are added to the reaction mixture which is sparged by bubbling N₂ into the mixture for 15 min. The reaction mixture is heated to 90° C. The DMF solution of 4-bromo-2,6-dimethylpyridine is added drop wise over 30 min and heating is continued overnight. The mixture is cooled to RT, MTBE (~2 L) is added, followed by water (1.5 L) and 30% aqueous NH₄OH (800 mL); the resulting mixture is stirred at RT for 30 min. The layers are separated, the aqueous layer is extracted once with MTBE (~2 L); the organic phases are combined, washed once with 10% aqueous NH₄OH (2 L), dried over Na₂SO₄, filtered, and the filtrate is evaporated under reduced pressure to obtain the crude title compound (153 g, 91.7% yield) as a pale yellow solid, contaminated with ~10% triphenylphosphine byproduct, which is suitable for use without additional purification. ¹H NMR (CDCl₃): δ 2.61 (s, 6H), 7.21 (s, 2H).

Preparation 13

1-(2,6-dimethylpyridin-4-yl)methamine dihydrochloride

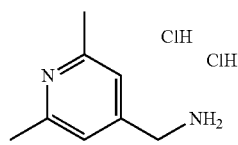

Scheme 4, step B: A solution of 2,6-dimethylpyridine-4-carbonitrile (2.26 g, 16.7 mmol) in EtOH (40 mL) is added to a suspension of 10% Pd on carbon (405 mg), EtOH (10 mL), and concentrated aqueous HCl (6.9 mL). The reaction vessel is evacuated, filled with nitrogen, and H$_2$ (55 psi) is introduced, with stirring of the subsequent reaction mixture at RT for 16 hr. The reaction mixture is filtered through diatomaceous earth. The filter cake is washed with MeOH and the combined filtrate/wash is concentrated to give a yellow solid. The crude material is triturated with boiling 30% EtOH/EtOAc, cooled to RT, and collected via filtration to give the title compound (2.64 g, 75% yield). LC-ES/MS (m/z): 137.0 (M+H).

Alternative Procedure for Preparation 13

1-(2,6-Dimethylpyridin-4-yl)methamine dihydrochloride

Scheme 4, step B: The following may be run in two batches and the two batches combined after the complete hydrogenation reaction: 2,6-Dimethylpyridine-4-carbonitrile (77.39 g, 527.0 mmol) is added to a 2 L Parr autoclave, equipped with a mechanical stirrer, containing a mixture of 10% Pd/C (45.8 g) in MeOH (800 mL) and a 4M solution of HCl in dioxane (500 mL). The autoclave is sealed, the resulting mixture is purged thoroughly with N$_2$ followed by H$_2$, and pressurized with H$_2$ to 60 psi with stirring at RT overnight. The reaction mixture is filtered and the filtrate is evaporated under reduced pressure. MeOH (~250 mL) is added to the resulting residue and stirred for 15 hr, and MTBE (2.5 L) is added slowly. The mixture is stirred at RT for 1 hr, filtered, and the solids are washed with MTBE (1 L). The solids are dried in vacuo at RT overnight to obtain the title compound as a pale yellow solid (217.0 g, 91.6% yield, combination of two runs), suitable for use without additional purification. LC-ES/MS (m/z): 137.2 (M+H), 92.5% purity, with 7.5% triphenylphosphine impurity present (1.57 min, m/z: 263.0).

Preparation 14

(3R)-3-[(1R)-1-(6-bromo-3-pyridyl)ethyl]-3-methyl-1H-pyrrolo[2,3-b]pyridin-2-one and (3S)-3-[(1R)-1-(6-bromo-3-pyridyl)ethyl]-3-methyl-1H-pyrrolo[2,3-b]pyridin-2-one

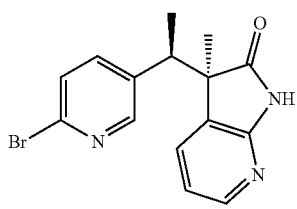

Major diastereomer

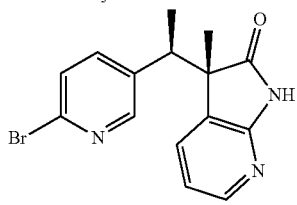

Minor diastereomer

Scheme 5, step A: A solution of 3-methyl-1,3-dihydropyrrolo[2,3-b]pyridin-2-one (109 g, 735.69 mmol) and [(1S)-1-(6-bromo-3-pyridyl)ethyl]methanesulfonate (207 g, 738.92 mmol) in anhydrous DMF (1100 mL) in a three-necked round bottom flask equipped with a mechanical stirrer, reflux condenser, and N$_2$ inlet is purged by bubbling N$_2$ over about 30 min. The resulting solution is cooled to 0° C. and Cs$_2$CO$_3$ (240 g, 736.59 mmol) is added portion wise. The mixture is additionally purged by bubbling N$_2$ for 15 min and stirred at about 0° C. for about 40 hr. The reaction mixture is diluted with water (4 L) and MTBE (3 L). The organic extract is washed sequentially with water and 5% aqueous LiCl, dried over Na$_2$SO$_4$, filtered and concentrated under reduced pressure to obtain the title compounds as a mixture of diastereomers (183.2 g, 75% yield) in ~5:1 ratio. LC-ES/MS (m/z for $^{79}$Br/$^{81}$Br): 332.0, 334.0 (M+H).

Preparation 15

(3R)-3-[(1R)-1-(6-bromo-3-pyridyl)ethyl]-3-methyl-1H-pyrrolo[2,3-b]pyridin-2-one, (7,7-dimethyl-2-oxo-norbornan-1-yl)methanesulfonic acid salt; (3R)-3-[(1R)-1-(6-bromo-3-pyridyl)ethyl]-3-methyl-1H-pyrrolo[2,3-b]pyridin-2-one, (1S)-(+)-10-camphorsulfonic acid salt

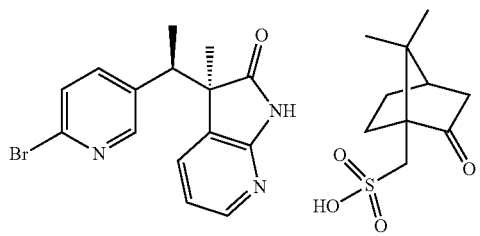 [SMILES: C[C@H](c1ccc(Br)nc1)[C@@]1(C)C(=O)Nc2ncccc21 ; CC1(C)C2CCC1(CS(=O)(=O)O)C(=O)C2]

Scheme 5, step B: A solution of a diastereomeric mixture of (3R)-3-[(1R)-1-(6-bromo-3-pyridyl)ethyl]-3-methyl-1H-pyrrolo[2,3-b]pyridin-2-one and (3S)-3-[(1R)-1-(6-bromo-3-pyridyl)ethyl]-3-methyl-1H-pyrrolo[2,3-b]pyridin-2-one (183.2 g, 553.5 mmol) in EtOAc (1.3 L) in a three-necked round bottom flask equipped with a mechanical stirrer, reflux condenser, and N$_2$ inlet is heated to 50° C. (1S)-(+)-10-camphorsulfonic acid (171.0 g, 736.1 mmol) is added and the reaction mixture is heated at reflux for 30 min, then cooled to RT and stirred overnight. The reaction mixture is filtered, the filter cake is washed with EtOAc, and the resulting white solid is dried under vacuum to obtain the title compound (288.3 g, 92.5% yield). LC-ES/MS (m/z for $^{79}$Br/$^{81}$Br): 332.0, 334.0 (M+H). Chiral HPLC (CHIRALPAK® AD-H, 4.6×150 mm, 100% EtOH containing 0.2% DMEA, 1 mL/min, 12 min run, 254 nm) of an EtOAc-extracted aliquot from a suspension in saturated aqueous NaHCO$_3$: $t_R$=7.66 min, >96% ee.

Preparation 16

(3R)-3-[(1R)-1-(6-bromo-3-pyridyl)ethyl]-3-methyl-1H-pyrrolo[2,3-b]pyridin-2-one

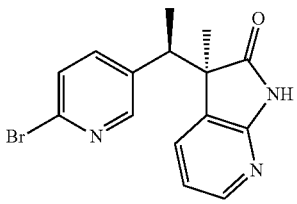 [SMILES: C[C@H](c1ccc(Br)nc1)[C@@]1(C)C(=O)Nc2ncccc21]

Scheme 5, step C: (3R)-3-[(1R)-1-(6-bromo-3-pyridyl)ethyl]-3-methyl-1H-pyrrolo[2,3-b]pyridin-2-one, (1S)-(+)-10-camphorsulfonic acid salt (288.3 g, 512.01 mmol) is stirred in a mixture of aqueous NaHCO₃ (371 g, 4416.4 mmol, 6 L H₂O) and 5 L EtOAc is added. The resulting biphasic mixture is stirred at RT for about 45 min, the layers are separated, and the aqueous phase is additionally extracted with EtOAc (4 L). The combined EtOAc phases are washed with saturated aqueous NaCl, dried over Na₂SO₄, filtered, and the filtrate is concentrated under reduced pressure. The resulting residue is crystallized from MeOH (~1.7 L), and the resulting solids are collected by filtration to obtain the title compound (244.4 g, 59.7% yield) as a white crystalline solid. LC-ES/MS (m/z for $^{79}Br/^{81}Br$): 332.0, 334.0 (M+H). Chiral HPLC (CHIRALPAK® AD-H, 4.6×150 mm, 100% EtOH containing 0.2% DMEA, 1 mL/min, 12 min run, 254 nm): $t_R$=7.66 min, >98% ee.

Preparation 17

2-ethyl-6-methylpyridine-4-carbonitrile

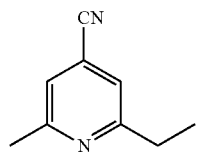

Scheme 8, step A: Ethylmagnesium bromide (18 ml, 17.7 mmol) is added in portions to a mixture of 2-chloro-6-methylisonicotinonitrile (Bioorganic & Medicinal Chemistry Letters, 20(2), 576-580; 2010) (1.5 g, 9.8 mmol), 1-methyl-2-pyrrolidinone (10 ml), THF (10 mL) and iron (III) acetoacetate (521 mg, 1.47 mmol) stirring under nitrogen at RT. The reaction mixture is concentrated to remove most of the THF and quenched with water. The aqueous layer is extracted with ethyl acetate. The combined organics are washed sequentially with water and saturated aqueous NaCl, dried over Na₂SO₄, filtered, and concentrated under reduced pressure to give crude product. The crude product is purified by flash chromatography on silica, eluting with 15% hexanes/ethyl acetate. The pure chromatography fractions are combined and concentrated under reduced pressure to give the title compound (0.53 g, 37%). LC-ES/MS (m/z): 147.2 (M+H).

Preparation 18

1-(2-ethyl-6-methylpyridin-4-yl)methanamine dihydrochloride

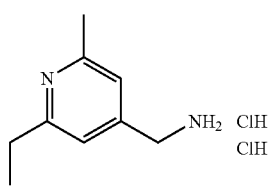

Scheme 8, step B: A solution of 2-ethyl-6-methylpyridine-4-carbonitrile (0.37 g, 2.5 mmol) in 2M NH₃ (2 mol/l) in MeOH (12.5 mL) is added to a suspension of Raney nickel (0.5 g) in 2M NH₃ in MeOH (12.5 mL). The reaction vessel is purged with nitrogen, and H₂ (60 psi) is introduced, with shaking of the subsequent reaction mixture at 40° C. for 15 minutes. The reaction mixture is re-pressurized with H₂ (60 psi) and continued to shake for 4 hr. The reaction mixture is filtered. The crude material is diluted with excess 3N HCl in MeOH and concentrated to give a green oil. The crude oil is triturated and concentrated sequentially in the following solvents: toluene, acetonitrile, methanol/toluene and acetonitrile/toluene, to give the title compound as a green solid after solvent removal. LC-ES/MS (m/z): 151.0 (M+H).

Preparation 19

2-cyclopropyl-6-methyl-pyridine-4-carbonitrile

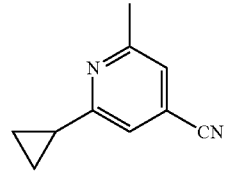

Scheme 8, step A: 2-Chloro-6-methyl-pyridne-4-carbonitrile (J. Med. Chem., 59(1), 313-327, 2016, 2.0 g, 12.7 mmol), cyclopropylboronic acid (1.84 g, 20.3 mmol), and K₃PO₄ (5.56 g, 25.4 mmol) are slurried in a mixture of toluene (40 mL) and water (2 mL). Pd(OAc)₂ (291 mg, 1.27 mmol) and tricyclohexylphosphine tetrafluoroborate (946 mg, 2.554 mmol) are added and the reaction mixture is heated under a balloon of nitrogen at 110° C. for 16 hr. The reaction mixture is cooled to RT, diluted with EtOAc (50 mL), and filtered over a bed of diatomaceous earth. The filtrate is washed with saturated aqueous NaCl, dried over Na₂SO₄, filtered, and concentrated under reduced pressure to give an amber oil. The resulting residue is purified by flash chromatography over silica, eluting with a gradient of 2-20% EtOAc in hexanes over 30 min, to give the title compound (1.66 g, 82% yield) as a light yellow solid after solvent evaporation. ¹H NMR (CDCl₃): δ 1.05-1.06 (m, 4H) 2.03-2.09 (m, 1H), 2.54 (s, 3H), 7.11 (s, 1H), 7.14 (s, 1H).

Preparation 20

(2-cyclopropyl-6-methyl-4-pyridyl)methanamine dihydrochloride

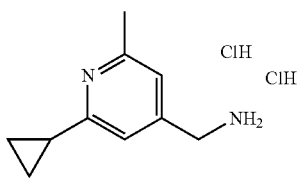

Scheme 8, step B: 2-Cyclopropyl-6-methyl-pyridine-4-carbonitrile (2.52 g, 15.9 mmol) is reduced in similar manner as described in Preparation 18 to give the title compound (3.57 g, 95% yield). LC-ES/MS (m/z): 163.0 (M+H).

Preparation 21

Methyl 2-isopropyl-6-methyl-pyridine-4-carboxylate

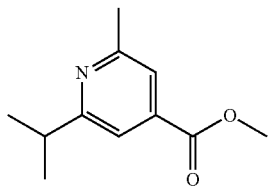

A THF solution of isopropyl magnesium chloride (2.0M, 7.53 mL, 15.1 mmol) is added drop wise, over 8 minutes, to a mixture of methyl 2-chloro-6-methyl-pyridine-4-carboxylate (1.92 g, 10.0 mmol), $MnCl_2$ (0.065 g, 0.502 mmol) and THF (25 mL) stirring under nitrogen in an ice/water bath. After stirring in the cold bath for 4 hr, the reaction is quenched with saturated aqueous $NH_4Cl$ and extracted with EtOAc (2×50 mL). The combined extract is washed with saturated aqueous NaCl, dried over $Na_2SO_4$, filtered, and concentrated under reduced pressure to give an amber oil. The crude product is purified by flash chromatography on silica, eluting with hexanes/ethyl acetate (gradient from 50:1 to 2:1). The pure chromatography fractions are combined and concentrated under reduced pressure to give the title compound (0.683 g, 35% yield). $^1H$ NMR ($CDCl_3$): δ 1.34 (d, J=6.9 Hz, 6H), 2.63 (s, 3H), 3.12-3.19 (m, 1H), 3.96 (s, 3H), 7.54 (s, 1H), 7.56 (s, 1H).

Preparation 22

2-[(2-isopropyl-6-methyl-4-pyridyl)methyl]isoindoline-1,3-dione

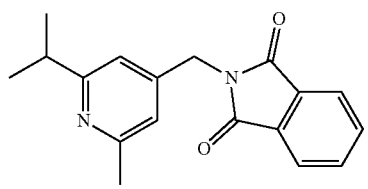 [SMILES: Cc1cc(CN2C(=O)c3ccccc3C2=O)cc(C(C)C)n1]

Sodium borohydride (0.231 g, 6.01 mmol) is added to a solution of methyl 2-isopropyl-6-methyl-pyridine-4-carboxylate (0.683 g, 3.53 mmol) in EtOH (15 mL) at RT. After stirring overnight, the solvent is removed under reduced pressure, the remaining oil diluted with saturated aqueous NaCl and extracted with EtOAc (2×50 mL). The combined extract is dried over $Na_2SO_4$, filtered, and concentrated under reduced pressure to give 652 mg of crude (2-isopropyl-6-methyl-4-pyridyl)methanol as an amber solid. The crude alcohol is dissolved in DCM (20 mL) and treated with thionyl chloride (0.514 mL, 7.02 mmol). After stirring at RT for 4 hr, the reaction mixture is concentrated under reduced pressure; dissolved in toluene and reconcentrated (2×). The crude alkyl chloride is dissolved in DMF (10 mL) and potassium phthalimide (1.32 g, 7.02 mmol) is added. The suspension is stirred at RT for 3.5 hr and diluted with water (100 mL). The resulting suspension is stirred at RT for one hour and the solid collected via filtration. The crude product is purified by flash chromatography on silica, eluting with DCM/ethyl acetate (gradient from 50:1 to 4:1). The pure chromatography fractions are combined and concentrated under reduced pressure to give the title compound (0.332 g, 32% yield). $^1H$ NMR ($CDCl_3$): δ 1.29 (d, J=6.9 Hz, 6H), 2.51 (s, 3H), 3.06-3.08 (m, 1H), 4.80 (s, 2H), 6.96 (s, 1H), 7.00 (s, 1H), 7.76-7.79 (m, 2H), 7.89-7.92 (m, 2H).

Preparation 23

(2-isopropyl-6-methyl-4-pyridyl)methanamine

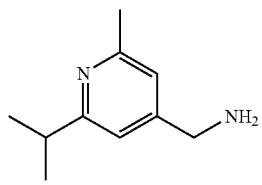

Hydrazine monohydrate (0.70 mL, 1.41 mmol) is added to a suspension of 2-[(2-isopropyl-6-methyl-4-pyridyl)methyl]isoindoline-1,3-dione (0.332 g, 1.13 mmol) and EtOH (10 mL) at RT. After refluxing for 1.5 hr, the reaction mixture is cooled to RT and the solids are removed by paper filtration. The filter cake is washed with EtOH (10 mL) and the combined filtrate/wash is concentrated under reduced pressure to give the title compound (0.179 g, 96% yield). $^1H$ NMR ($CDCl_3$): δ 1.31 (d, J=6.8 Hz, 6H), 1.56-1.63 (bs, 2H), 2.54 (s, 3H), 3.02-3.09 (m, 1H), 3.86 (s, 2H), 6.95 (s, 2H).

Preparation 24

2-cyclobutyl-6-methyl-pyridine-4-carbonitrile

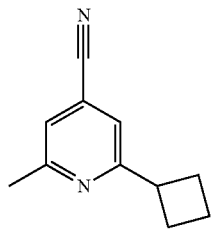

Scheme 8, step A: Add cyclobutylzinc bromide (0.5M in THF, 3.28 mmol) drop wise to a degassed solution of 2-chloro-6-methyl-pyridine-4-carbonitrile (1.64 mmol,) and [1,1'-bis(diphenylphosphino)ferrocene]dichloropalladium (II) (0.164 mmol) in 1,4-dioxane. Heat to 80° C. for 1 hr then cool to RT. Add water (5 mL) and stir rapidly for 5 minutes. Remove the solids by filtration through diatomaceous earth. Wash with EtOAc and separate the layers. Wash the organic layer with water and saturated aqueous NaCl. Dry over $Na_2SO_4$, filter, and concentrate under reduced pressure. Purify the resulting residue by flash chromatography on silica gel, eluting with a gradient of 10-30% EtOAc in heptane, to give the title compound (232 mg, 82%), after solvent evaporation. LC-ES/MS (m/z): 173.0 (M+H).

Preparation 25

(2-cyclobutyl-6-methyl-4-pyridyl)methanamine dihydrochloride

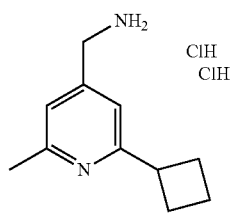

Scheme 8, step B: Prepare the title compound essentially by the method described in Preparation 18, using 2-cyclobutyl-6-methyl-pyridine-4-carbonitrile. LC-ES/MS (m/z): 177.0 (M+H).

Preparation 26

2-cyclopentyl-6-methyl-pyridine-4-carbonitrile

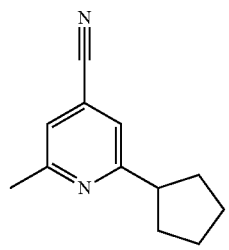

Scheme 8, step A: Prepare the title compound essentially by the method described in Preparation 24, using cyclopentylzinc bromide. $^1$H NMR (CDCl$_3$): δ 1.62-1.78 (m, 4H), 1.78-1.89 (m, 2H), 2.00-2.14 (m, 2H), 2.57 (s, 3H), 3.09-3.25 (m, 1H), 7.16 (s, 1H), 7.19 (s, 1H).

Preparation 27

(2-cyclopentyl-6-methyl-4-pyridyl)methanamine

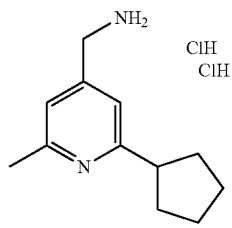

Scheme 8, step B: Prepare the title compound essentially by the method described in Preparation 18, using 2-cyclopenyl-6-methyl-pyridine-4-carbonitrile. LC-ES/MS (m/z): 191.0 (M+H).

Preparation 28

4-chloro-7-(2,4-dimethoxybenzyl)-5-methyl-5,7-dihydro-6H-pyrrolo[2,3-d]pyrimidin-6-one

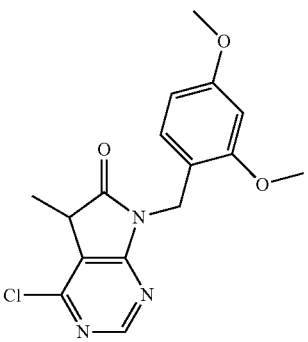 [SMILES: COc1ccc(CN2C(=O)C(C)c3c(Cl)ncnc32)c(OC)c1]

Scheme 7, step A: To a solution of 4-chloro-7-(2,4-dimethoxybenzyl)-5,7-dihydro-6H-pyrrolo[2,3-d]pyrimidin-6-one (US 2010/0120801, 6.02 g, 18.8 mmol) in DMF (37.7 mL) is added NaH (60% in mineral oil, 753 mg, 18.8 mmol) slowly. The reaction mixture is stirred at RT for 30 min. CH$_3$I (1.17 mL, 18.8 mmol) is added drop wise, and the reaction mixture is stirred at RT for 30 min. Saturated aqueous NH$_4$Cl and EtOAc are added and the layers are separated. The organic layer is washed with brine, dried over Na$_2$SO$_4$, filtered, and concentrated under reduced pressure to give a solid residue. The residue is purified by flash chromatography over silica, eluting with hexanes/EtOAc (gradient from 9:1 to 1:1) to give the title compound (1.30 g, 20%), after solvent evaporation. LC-ES/MS (m/z $^{35}$Cl/$^{37}$Cl): 334.0/336.0 (M+H).

Preparation 29

Methyl 4-[(1S)-1-hydroxyethyl]benzoate

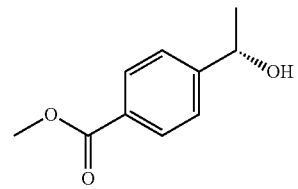

Palladium(II) acetate (335 mg, 1.49 mmol), 1,1'-bis(diphenylphosphino)ferrocene (993 mg, 1.79 mmol), (1S)-1-(4-bromophenyl)ethanol (3.0 g, 14.9 mmol), anhydrous ACN (100 mL), anhydrous MeOH (70 mL), and TEA (5.2 mL, 37 mmol) are combined in a 300 mL Parr autoclave with a mechanical stirrer. The autoclave is sealed, purged with CO$_2$, pressurized to 689 kPa with CO$_2$, and heated to 100° C. with stirring. After 6 hr at 100° C., the reaction mixture is cooled to room temperature and filtered. The filtrate is concentrated under reduced pressure to give a solid residue. The residue is purified by flash chromatography over silica, eluting with hexanes/EtOAc (gradient from 9:1 to 1:1) to give the title compound (2.7 g, 100%), after solvent evaporation. LC-ES/MS (m/z): 181.2 (M+H).

Preparation 30

Methyl 4-{(1S)-1-[(methylsulfonyl)oxy]ethyl}benzoate

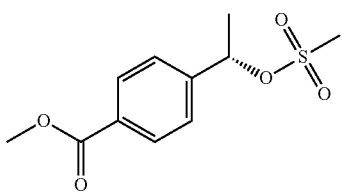

To a stirred solution of methyl 4-[(1S)-1-hydroxyethyl]benzoate (6.16 g, 34.2 mmol) and TEA (7.15 mL, 51.3 mmol) in DCM (51 mL) at 0° C. is added methanesulfonyl chloride (3.17 mL, 41.0 mmol). After 1 hr at 0° C., water and DCM are added and the layers are separated. The aqueous layer is extracted with DCM. The organic layers are combined and washed sequentially with saturated aqueous NaHCO$_3$ and then saturated NaCl; dried over Na$_2$SO$_4$; filtered, and concentrated under reduced pressure to give the title compound (8.71 g, 99% yield). $^1$H NMR (CDCl$_3$) δ 1.73 (d, J=6.7 Hz, 3H), 2.80 (s, 3H), 3.93 (s, 3H), 5.77 (q, J=6.7 Hz, 1H), 7.47-7.49 (m, 2H), 8.06-8.09 (m, 2H).

Preparation 31

Methyl 4-{(1R)-1-[(5R)-4-chloro-7-(2,4-dimethoxybenzyl)-5-methyl-6-oxo-6,7-dihydro-5H-pyrrolo[2,3-d]pyrimidin-5-yl]ethyl}benzoate

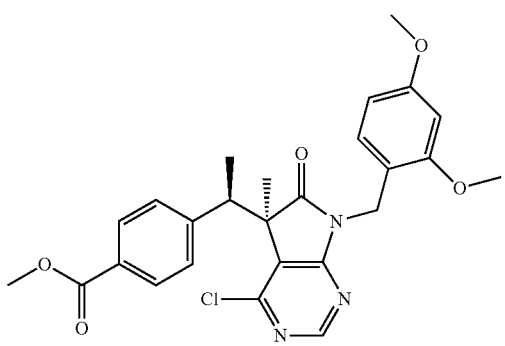

Scheme 7, step B (X=CH): To a stirred solution of 4-chloro-7-(2,4-dimethoxybenzyl)-5-methyl-5,7-dihydro-6H-pyrrolo[2,3-d]pyrimidin-6-one (3.68 g, 10.9 mmol) and methyl 4-{(1S)-1-[(methylsulfonyl)oxy]ethyl}benzoate (2.82 g, 10.9 mmol) in DMF (54.5 mL) under nitrogen at 0° C. is added Cs$_2$CO$_3$ (4.26 g, 13.1 mmol). The reaction mixture is thoroughly purged with nitrogen and gradually warmed from 0° C. to RT with stirring over 19 hr. DCM and saturated aqueous NaHCO$_3$ are added and the layers are separated. The aqueous layer is extracted again with DCM. The organic layers are combined, dried over Na$_2$SO$_4$, filtered, and concentrated under reduced pressure to give a residue. The crude product is purified by flash chromatography over silica, eluting with hexanes/EtOAc (gradient from 1:0 to 1:1). The pure chromatography fractions are combined to give the title compound (3.38 g, 61% yield) as a 15:1 ratio of diastereomers after solvent evaporation. LC-ES/MS (m/z $^{35}$Cl/$^{37}$Cl): 496.0/498.0 (M+H).

The impure chromatography fractions are concentrated under reduced pressure and repurified by flash chromatography over silica, eluting with DCM/EtOAc (gradient from 1:0 to 9:1) to give additional title compound (991 mg, 18%) as a 5:1 ratio of diastereomers after solvent evaporation. LC-ES/MS (m/z $^{35}$Cl/$^{37}$Cl): 496.0/498.0 (M+H).

Preparation 32

Methyl 4-{(1R)-1-[(5R)-7-(2,4-dimethoxybenzyl)-5-methyl-6-oxo-6,7-dihydro-5H-pyrrolo[2,3-d]pyrimidin-5-yl]ethyl}benzoate

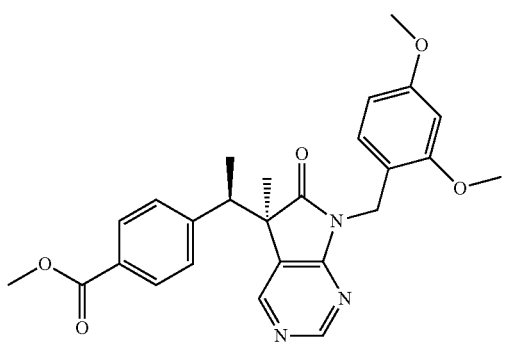

Scheme 7, step C (X=CH): Palladium (5% on carbon, 24 mg, 0.23 mmol), methyl 4-{(1R)-1-[(5R)-4-chloro-7-(2,4-dimethoxybenzyl)-5-methyl-6-oxo-6,7-dihydro-5H-pyrrolo[2,3-d]pyrimidin-5-yl]ethyl}benzoate (0.2 g, 0.4 mmol, 15:1 dr), anhydrous MeOH (10 mL), and TEA (0.2 mL, 1 mmol) are combined in a 70 mL Parr shaker. The Parr shaker is sealed, purged with N$_2$, purged with H$_2$, and pressurized to 138 kPa with H$_2$. The reaction mixture is shaken at RT for 70 min and then the reaction mixture is filtered.

Palladium (5% on carbon, 294 mg, 2.76 mmol), methyl 4-{(1R)-1-[(5R)-4-chloro-7-(2,4-dimethoxybenzyl)-5-methyl-6-oxo-6,7-dihydro-5H-pyrrolo[2,3-d]pyrimidin-5-yl]ethyl}benzoate (3.1 g, 6.0 mmol, 15:1 dr), anhydrous MeOH (150 mL), and TEA (2.0 mL, 14.3 mmol) are combined in a 500 mL Parr shaker. The Parr shaker is sealed, purged with N$_2$, purged with H$_2$, and pressurized to 138 kPa with H$_2$. The reaction mixture is shaken at RT for 80 min and then the reaction mixture is filtered. Both filtrates from the hydrodechlorination reactions are combined and concentrated under reduced pressure to give a residue.

Palladium (5% on carbon, 0.10 g, 0.94 mmol), methyl 4-{(1R)-1-[(5R)-4-chloro-7-(2,4-dimethoxybenzyl)-5-methyl-6-oxo-6,7-dihydro-5H-pyrrolo[2,3-d]pyrimidin-5-yl]ethyl}benzoate (991 mg, 1.93 mmol, 5:1 dr), anhydrous MeOH (50 mL), and TEA (0.70 mL, 5.0 mmol) are combined in a 500 mL Parr shaker. The Parr shaker is sealed, purged with N$_2$, purged with H$_2$, and pressurized to 138 kPa with H$_2$. The reaction mixture is shaken at RT for 85 min and then the reaction mixture is filtered. The filtrate is concentrated under reduced pressure to give a residue.

All residues from the hydrodechlorination reactions above are dissolved in DCM and combined. Saturated aqueous NaHCO$_3$ is added and the layers are separated. The aqueous layer is extracted twice with DCM. The organic layers are combined, dried over Na$_2$SO$_4$, filtered, and concentrated under reduced pressure to give a solid residue. The residue is purified by flash chromatography over silica, eluting with hexanes/EtOAc (gradient from 4:1 to 0:1). The impure chromatography fractions are concentrated under reduced pressure and repurified by flash chromatography over silica, eluting with hexanes/EtOAc (gradient from 3:1 to 0:1). All of the pure chromatography fractions are combined and concentrated under reduced pressure to give the title compound (2.99 g, 74% yield) as a single diastereomer after solvent evaporation. LC-ES/MS (m/z): 462.2 (M+H). $^1$H NMR (CDCl$_3$) δ 1.18 (d, J=7.1 Hz, 3H), 1.39 (s, 3H), 3.35 (q, J=7.1 Hz, 1H), 3.74 (s, 3H), 3.79 (s, 3H), 3.92 (s, 3H), 4.87 (d, J=14.9 Hz, 1H), 4.92 (d, J=14.9 Hz, 1H), 6.38 (dd, J=2.4, 8.4 Hz, 1H), 6.41 (d, J=2.4 Hz, 1H), 7.01 (d, J=8.4 Hz, 1H), 7.12-7.17 (m, 2H), 7.88-7.92 (m, 2H), 7.94 (s, 1H), 8.78 (s, 1H).

Preparation 33

Methyl 4-{(1R)-1-[(5R)-5-methyl-6-oxo-6,7-dihydro-5H-pyrrolo[2,3-d]pyrimidin-5-yl]ethyl}benzoate

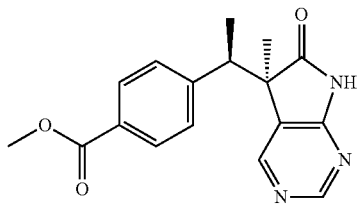 [SMILES: COC(=O)c1ccc([C@@H](C)[C@@]2(C)C(=O)Nc3ncncc32)cc1]

Scheme 7, step D (X=CH): A solution of methyl 4-{(1R)-1-[(5R)-7-(2,4-dimethoxybenzyl)-5-methyl-6-oxo-6,7-dihydro-5H-pyrrolo[2,3-d]pyrimidin-5-yl]ethyl}benzoate (1.50 g, 3.25 mmol) in anisole (1.77 mL, 16.3 mmol) and TFA (4.92 mL, 65.0 mmol) at RT is divided into five equal portions and each portion is placed into a 4 mL vial. The vials are capped tightly and heated to 120° C. with stirring. After 6 hr, the reaction mixtures are cooled to RT. The contents of all of the vials are poured into a mixture of DCM and saturated aqueous NaHCO$_3$ and the layers are separated. The aqueous layer is extracted twice with DCM. The organic layers are combined, dried over Na$_2$SO$_4$, filtered, and concentrated under reduced pressure to give a residue. The residue is purified by flash chromatography over silica, eluting with DCM/EtOAc (gradient from 1:0 to 0:1) to give the title compound (495 mg, 49% yield), after solvent evaporation. LC-ES/MS (m/z): 312.0 (M+H).

Preparation 34

4-{(1R)-1-[(5R)-5-methyl-6-oxo-6,7-dihydro-5H-pyrrolo[2,3-d]pyrimidin-5-yl]ethyl}benzoic acid

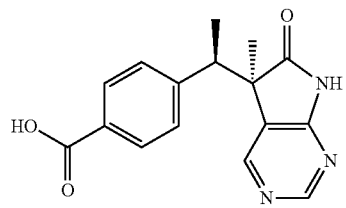

Scheme 7, step E (X=CH): To a solution of methyl 5-{(1R)-1-[(3R)-3-methyl-2-oxo-2,3-dihydro-1H-pyrrolo[2,3-b]pyridin-3-yl]ethyl}pyridine-2-carboxylate (480 mg, 1.54 mmol) in THF (7.7 mL) at RT is added a solution of LiOH (111 mg, 4.63 mmol) in water (1.54 mL). After 18 hr, the reaction mixture is diluted with DCM and saturated aqueous NaCl. 1.0 M HCl is added slowly at RT until the mixture reaches pH ~2. The layers are separated, and the aqueous layer is extracted three times with CHCl$_3$/2-propanol (3:1). The organic layers are combined, dried over Na$_2$SO$_4$, filtered, and concentrated under reduced pressure to give the title compound (449 mg, 98% yield). LC-ES/MS (m/z): 298.0 (M+H).

Preparation 35

1-(2,6-dimethylpyridin-4-yl)methanamine

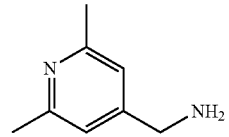

A solution of 2,6-dimethylpyridine-4-carbonitrile (2.0 g, 15.1 mmol) in 2.0 M NH$_3$ in MeOH (75 mL) is added to a suspension of Raney nickel (0.5 g, 9 mmol) in 2.0 M NH$_3$ in MeOH (75 mL) in a 500 mL Parr shaker. The Parr shaker is sealed, purged with N$_2$, purged with H$_2$, and pressurized to 414 kPa with H$_2$. The reaction mixture is heated to 40° C. and allowed to cool slowly to RT while being shaken for 18 hr. The reaction mixture is filtered and concentrated under reduced pressure to give a green residue. The residue is purified by flash chromatography over silica, eluting with hexanes/DCM/IPAm (gradient from 9:0:1 to 6:3:1). The product-containing chromatography fractions are concentrated under reduced pressure and repurified by flash chromatography over silica, eluting with hexanes/DCM/IPAm (45:45:10) to give the title compound (1.02 g, 49% yield), after solvent evaporation. LC-ES/MS (m/z): 137.0 (M+H).

Preparation 36

Methyl 5-[(1S)-1-hydroxyethyl]pyridine-2-carboxylate

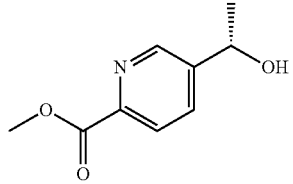

Palladium(II) acetate (180 mg, 0.762 mmol), 1,1'-bis(diphenylphosphino)ferrocene (535 mg, 0.936 mmol), (1S)-1-(6-bromo-3-pyridyl)ethanol (1.6 g, 7.9 mmol), anhydrous MeOH (40 mL), anhydrous ACN (60 mL), and TEA (2.8 mL, 20 mmol) are combined in a 300 mL Parr autoclave with a mechanical stirrer. The autoclave is sealed, purged with CO, pressurized to 689 kPa with CO, and heated to 85° C. with stirring. After 2 hr, the reaction mixture is cooled to RT and filtered. The filtrate is concentrated under reduced pressure to give an oil. The residue is purified by flash chromatography over silica, eluting with hexanes/EtOAc to give the title compound (1.5 g, 100% yield). LC-ES/MS (m/z): 182.0 (M+H).

Preparation 37

Methyl 5-[(1S)-1-methylsulfonyloxyethyl]pyridine-2-carboxylate

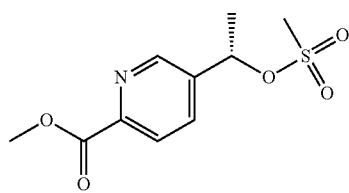 [SMILES: COC(=O)c1ccc([C@H](C)OS(C)(=O)=O)cn1]

Methyl 5-[(1S)-1-hydroxyethyl]pyridine-2-carboxylate (1.5 g, 8.3 mmol) is stirred in DCM (20 mL) with TEA (1.7 mL, 12 mmol) at 0° C. Methanesulfonyl chloride (0.78 mL, 9.9 mmol) is added drop wise and stirred for 2 hr. The solution is diluted with DCM, washed with NaHCO$_3$ and saturated aqueous NaCl, then dried over Na$_2$SO$_4$, filtered, and concentrated to give the title compound (2.1 g, 100% yield). $^1$H NMR (CDCl$_3$) δ 1.77 (d, J=6.7 Hz, 3H), 2.93 (s, 3H), 4.03 (s, 3H), 5.85 (q, J=6.7 Hz, 1H), 7.91 (dd, J=2.2, 8.1 Hz, 1H), 8.18 (d, J=8.1 Hz, 1H), 8.76 (d, J=2.2 Hz, 1H).

Preparation 38

Methyl 5-[(1R)-1-[(5R)-4-chloro-7-[(2,4-dimethoxyphenyl)methyl]-5-methyl-6-oxo-pyrrolo[2,3-c]pyrimidin-5-yl]ethyl]pyridine-2-carboxylate

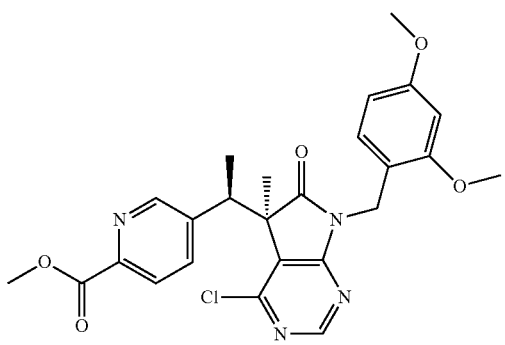

Scheme 7, step B (X=N): 4-Chloro-7-[(2,4-dimethoxyphenyl)methyl]-5-methyl-5H-pyrrolo[2,3-c]pyridazin-6-one (2.0 g, 6.0 mmol) and methyl 5-[(1S)-1-methylsulfonyloxyethyl]pyridine-2-carboxylate (1.86 g, 7.2 mmol) are combined in DMF (50 ml), cooled to 0° C. and thoroughly purged with nitrogen. Cesium carbonate (2.35 g, 1.2 mmol) is added, and the mixture is thoroughly purged with nitrogen and stirred overnight at 0° C. The reaction solution is diluted with EtOAc and washed with water and saturated aqueous NaCl. The organic layer is dried over Na$_2$SO$_4$, filtered, and concentrated under reduced pressure. The crude product is purified by flash chromatography over silica, eluting with hexanes/EtOAc to obtain the title compound (2.3 g, 77% yield). LC-ES/MS (m/z): 497.0 (M+H).

Preparation 39

Methyl 5-[(1R)-1-[(5R)-7-[(2,4-dimethoxyphenyl)methyl]-5-methyl-6-oxo-pyrrolo[2,3-d]pyrimidin-5-yl]ethyl]pyridine-2-carboxylate

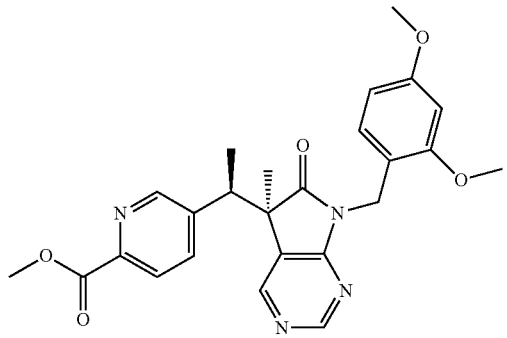

Scheme 7, step C (X=N): Palladium (5% on carbon, 240 mg, and 2.4 mmol) is added to a 500 mL Parr autoclave and purged with nitrogen. Methyl 5-[(1R)-1-[(5R)-4-chloro-7-[(2,4-dimethoxyphenyl)methyl]-5-methyl-6-oxo-pyrrolo[[2,3-c]pyrimidin-5-yl]ethyl]pyridine-2-carboxylate (2.2 g, 4.4 mmol) and MeOH (100 mL) are added, the autoclave sealed, and purged with nitrogen followed by hydrogen. The autoclave is pressurized with hydrogen to 414 kPa and shaken for 4 hr at RT. The reaction solution is filtered and concentrated under reduced pressure to give the title compound (2.1 g, 100% yield). LC-ES/MS (m/z): 463.2 (M+H).

Preparation 40

Methyl 5-[(1R)-1-[(5R)-5-methyl-6-oxo-7H-pyrrolo[2,3-d]pyrimidin-5-yl]ethyl]pyridine-2-carboxylate

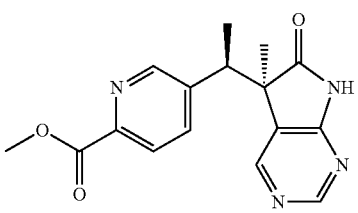 [SMILES: COC(=O)c1ccc([C@@H](C)[C@@]2(C)C(=O)Nc3ncncc32)cn1]

Scheme 7, step D (X=N): Methyl 5-[(1R)-1-[(5R)-7-[(2,4-dimethoxyphenyl)methyl]-5-methyl-6-oxo-pyrrolo[2,3-d]pyrimidin-5-yl]ethyl]pyridine-2-carboxylate (750 mg, 1.62 mmol) is combined in a microwave vial with anisole (2.5 mL, 23 mmol) and trifluoroacetic acid (2.5 mL, 32 mmol). The vial is capped and heated in a microwave at 140° C. for 3 hr. The solution is diluted with CH$_2$Cl$_2$ and washed with NaHCO$_3$. The organic layer is dried over Na$_2$SO$_4$, filtered and concentrated under reduced pressure. The crude product is purified by flash chromatography over silica, eluting with CH$_2$Cl$_2$/EtOAc/MeOH to obtain the title compound (250 mg, 49% yield). LC-ES/MS (m/z): 313.0 (M+H).

Preparation 41

5-[(1R)-1-[(5R)-5-methyl-6-oxo-7H-pyrrolo[2,3-d]pyrimidin-5-yl]ethyl]pyridine-2-carboxylic acid

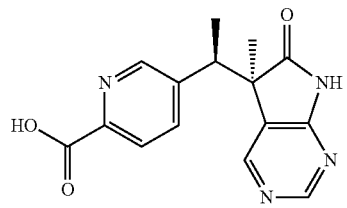 [SMILES: C[C@H](c1ccc(C(=O)O)nc1)[C@@]1(C)C(=O)Nc2ncncc21]

Scheme 7, step E (X=N): To a solution of methyl 5-[(1R)-1-[(5R)-5-methyl-6-oxo-7H-pyrrolo[2,3-d]pyrimidin-5-yl]ethyl]pyridine-2-carboxylate (250 mg, 0.80 mmol) in THF (5 mL) and water (1 mL) at RT is added LiOH (58 mg, 2.4 mmol). The reaction mixture is stirred for 48 hr at RT. The mixture is diluted with DCM (10 mL) and 1M HCl is added to reach pH ~3. Saturated aqueous NaCl is added and the mixture is extracted three times with CHCl$_3$/iPrOH (3:1). The organic layers are combined and dried over Na$_2$SO$_4$, filtered, and concentrated under reduced pressure to give the title compound (188 mg, 79% yield). LC-ES/MS (m/z): 297.0 (M+H).

Preparation 42

Methyl 2-isopropyl-6-methyl-pyridine-4-carboxylate

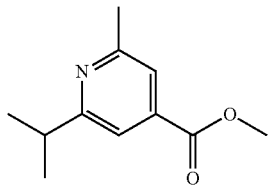

A 2M solution of isopropyl magnesium chloride in THF (7.53 mL, 15.1 mmol) is added drop wise, over 8 minutes, to a mixture of methyl 2-chloro-6-methyl-pyridine-4-carboxylate (1.92 g, 10.0 mmol), MnCl$_2$ (65 mg, 0.5 mmol) and THF (25 mL), stirring under nitrogen in an ice/water bath. After stirring in the cold bath for 4 hours, the reaction is quenched with saturated aqueous NH$_4$Cl and extracted with EtOAc (2×50 mL). The combined extracts are washed with saturated aqueous NaCl, dried over Na$_2$SO$_4$, filtered, and concentrated under reduced pressure to give an amber oil. The crude product is purified by flash chromatography on silica, eluting with hexanes/ethyl acetate (gradient from 50:1 to 2:1). The pure chromatography fractions are combined and concentrated under reduced pressure to give the title compound (0.683 g, 35% yield). $^1$H NMR (CDCl$_3$): δ 1.34 (d, J=6.9 Hz, 6H) 2.63 (s, 3H), 3.12-3.19 (m, 1H), 3.96 (s, 3H), 7.54 (s, 1H), 7.56 (s, 1H).

Preparation 43

2-[(2-isopropyl-6-methyl-4-pyridyl)methyl]isoindoline-1,3-dione

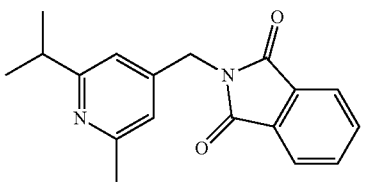 [SMILES: Cc1cc(CN2C(=O)c3ccccc3C2=O)cc(C(C)C)n1]

Sodium borohydride (231 mg, 6.0 mmol) is added to a solution of methyl 2-isopropyl-6-methyl-pyridine-4-carboxylate (683 mg, 3.53 mmol) in EtOH (15 mL) at RT. After stirring overnight, the solvent is removed under reduced pressure, the remaining oil diluted with saturated aqueous NaCl and extracted with EtOAc (2×50 mL). The combined extracts are dried over Na$_2$SO$_4$, filtered, and concentrated under reduced pressure to give 652 mg of crude (2-isopropyl-6-methyl-4-pyridyl)methanol as an amber solid. The crude alcohol is dissolved in DCM (20 mL) and treated with thionyl chloride (0.51 mL, 7.02 mmol). After stirring at RT for 4 hr, the reaction mixture is concentrated under reduced pressure, dissolved in toluene, and reconcentrated (2×). The crude alkyl chloride is dissolved in DMF (10 mL) and potassium phthalimide (1.32 g, 7.02 mmol) is added. The suspension is stirred at RT for 3.5 hours and diluted with water (100 mL). The resulting suspension is stirred at RT for 1 hr and the solid collected via filtration. The crude product is purified by flash chromatography on silica, eluting with DCM/ethyl acetate (gradient from 50:1 to 4:1). The pure chromatography fractions are combined and concentrated under reduced pressure to give the title compound (332 mg, 32% yield). $^1$H NMR (CDCl$_3$): δ 1.29 (d, J=6.9 Hz, 6H) 2.51 (s, 3H), 3.06-3.08 (m, 1H), 4.80 (s, 2H), 6.96 (s, 1H), 7.00 (s, 1H), 7.76-7.79 (m, 2H), 7.89-7.92 (m, 2H).

Preparation 44

(2-isopropyl-6-methyl-4-pyridyl)methanamine

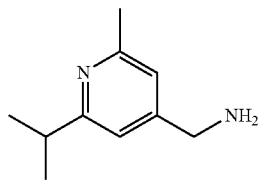

Hydrazine monohydrate (0.7 mL, 1.41 mmol) is added to a suspension of 2-[(2-isopropyl-6-methyl-4-pyridyl)methyl]isoindoline-1,3-dione (332 mg, 1.13 mmol) and EtOH (10 mL) at RT. After refluxing for 1.5 hours, the reaction mixture is cooled to RT and the solids are removed by paper filtration. The filter cake is washed with EtOH (10 mL) and the combined filtrate/wash is concentrated under reduced pressure to give the title compound (0.179 g, 96% yield). $^1$H NMR (CDCl$_3$): δ 1.31 (d, J=6.8 Hz, 6H), 1.56-1.63 (br-s, 2H), 2.54 (s, 3H), 3.02-3.09 (m, 1H), 3.86 (s, 2H), 6.95 (s, 2H).

Preparation 45

(6-chloro-4-methyl-2-pyridyl)methanol

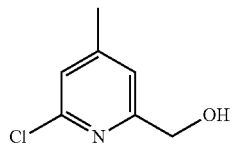

Sodium borohydride (905 mg, 23.4 mmol) is added in one portion to a solution of ethyl 6-chloro-4-methylpyridine-2-carboxylate (2.81 g, 13.8 mmol) dissolved in EtOH (25 mL). The reaction mixture is stirred for 18 hr at RT and concentrated under reduced pressure. The resulting residue is diluted with saturated aqueous NaCl and extracted twice with EtOAc, the organic extracts are dried over $Na_2SO_4$, filtered, and concentrated under reduced pressure to obtain the title compound suitable for use without additional purification. LC-ES/MS (m/z $^{35}Cl/^{37}Cl$): 158.0/160.0 (M+H).

Preparation 46

2-chloro-6-(chloromethyl)-4-methyl-pyridine

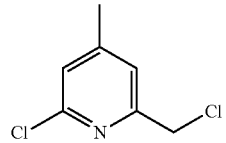

To a solution of (6-chloro-4-methyl-2-pyridyl)methanol (2.3 g, 13.8 mmol) in DCM (25 mL) under an atmosphere of nitrogen is added thionyl chloride (2 mL, 27.5 mmol). The reaction mixture is stirred at RT for 4.5 hr, concentrated under reduced pressure, and the residue reconstituted in toluene and reconcentrated twice more under reduced pressure, then dried in a vacuum oven at 45° C. overnight, to obtain the title compound (2.36 g, 97% yield) as a light amber oil. $^1$H NMR (CDCl$_3$): δ 2.37 (s, 3H), 4.59 (s, 2H), 7.11 (s, 1H), 7.24 (s, 1H).

Preparation 47

2-[(6-chloro-4-methyl-2-pyridyl)methyl]isoindoline-1,3-dione

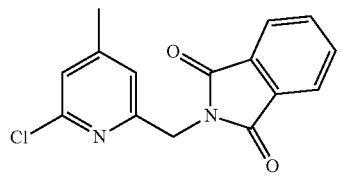 [SMILES: Cc1cc(Cl)nc(CN2C(=O)c3ccccc3C2=O)c1]

Potassium phthalimide (2.98 g, 15.8 mmol) is added to a solution of 2-chloro-6-(chloromethyl)-4-methyl-pyridine (2.36 g, 13.1 mmol) in DMF (25 mL) under a stream of nitrogen at RT. Stirring is continued for 3.5 hr, and additional potassium phthalimide (523 mg, 2.8 mmol) is added as stirring at RT is continued over 72 hr. The reaction mixture is diluted with water (150 mL) and the mixture is stirred for 30 min. The resulting white precipitate is collected by vacuum filtration, and the solids are dried in a vacuum oven at 35° C. overnight to obtain the title compound as a white solid (3.6 g, 96% yield). $^1$H NMR (CDCl$_3$): δ 2.29 (s, 3H), 4.94 (s, 2H), 6.92 (s, 1H), 7.04 (s, 1H), 7.73-7.79 (m, 2H), 7.88-7.93 (m, 2H).

Preparation 48

6-[(1,3-dioxoisoindolin-2-yl)methyl]-4-methy-pyridine-2-carbonitrile

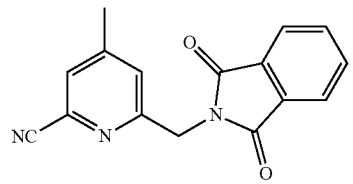 [SMILES: Cc1cc(C#N)nc(CN2C(=O)c3ccccc3C2=O)c1]

Nitrogen is bubbled through a suspension of 2-[(6-chloro-4-methyl-2-pyridyl)methyl]isoindoline-1,3-dione (1.3 g, 4.6 mmol), zinc cyanide (420 mg, 3.5 mmol), [1,1'-bis(diphenylphosphino)ferrocene]palladium(II) dichloride (174 mg, 0.23 mmol) and elemental zinc (76 mg, 1.2 mmol) in DMF (20 mL) for 10 min. The reaction mixture is heated in an oil bath at 120° C. for 5.5 hr. The mixture is cooled to RT, diluted with EtOAc (100 mL), and filtered through paper to remove any insolubles. The filtrate is washed sequentially with 15% aqueous NH$_4$OH, water, and saturated aqueous NaCl; the organic layer is dried over Na$_2$SO$_4$, filtered, and concentrated under reduced pressure. The resulting residue is purified by flash chromatography on silica gel, eluting with 10-60% EtOAc in hexanes over 35 min to obtain the title compound (1.04 g, 80.5% yield) as a light yellow solid after solvent evaporation. $^1$H NMR (CDCl$_3$): δ 2.39 (s, 3H), 5.00 (s, 2H), 7.28 (s, 1H), 7.40 (s, 1H), 7.74-7.80 (m, 2H), 7.88-7.94 (m, 2H).

Preparation 49

6-(aminomethyl)-4-methyl-pyridine-2-carbonitrile dihydrochloride

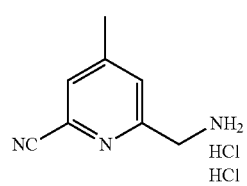

Hydrazine hydrate (371 μL, 7.5 mmol) is added to a suspension of 6-[(1,3-dioxoisoindolin-2-yl)methyl]-4-methyl-pyridine-2-carbonitrile (1.04 g, 3.7 mmol) in EtOH (20 mL) and the resulting mixture is heated at reflux for 1.5 hr. The reaction mixture is cooled, filtered, and the filtrate is concentrated under reduced pressure. The resulting residue is dissolved in MeOH (~25 mL) and loaded onto an SCX column (10 g), eluting with 1:1 MeOH:DCM (30 mL), MeOH (20 mL), and 2M NH$_3$/MeOH (50 mL). The methanolic ammonia fractions are concentrated under reduced pressure to give a light yellow oil which is dissolved in THF (15 mL) and treated with 4N HCl in 1,4-dioxane (2.5 mL). The mixture is stirred at RT for 15 min, and the resulting solids are collected by vacuum filtration. The crystalline filter cake is dried in a vacuum oven at 45° C. overnight to obtain the title compound (541 mg, 66% yield) as a pale yellow solid. $^1$H NMR (DMSO-d$_6$): δ 2.41 (s, 3H), 4.22 (q, J=5.6 Hz, 2H), 7.70 (s, 1H), 7.95 (s, 1H), 8.55 (br-s, 2H).

Preparation 50

(2-chloro-6-methylpyridin-4-yl)methanol

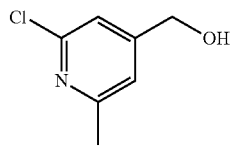

Prepare from methyl 2-chloro-6-methylpyridine-4-carboxylate (2.4 g, 12.5 mmol) essentially by the method described in Preparation 45 to obtain the title compound (2.0 g, 97% yield). $^1$H NMR (CDCl$_3$): δ 2.54 (s, 3H), 4.71 (s, 2H), 7.07 (s, 1H), 7.16 (s, 1H).

Preparation 51

2-chloro-4-(chloromethyl)-6-methylpyridine

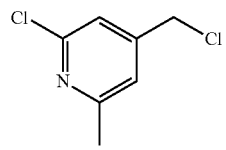

Prepare from (2-chloro-6-methylpyridin-4-yl)methanol (1.97 g, 12.1 mmol) essentially by the method described in Preparation 46 to obtain the title compound (2.28 g, 99.5% yield). $^1$H NMR (DMSO-d$_6$): δ 2.45 (s, 3H), 4.74 (s, 2H), 7.33 (s, 1H), 7.37 (s, 1H).

Preparation 52

2-[(2-chloro-6-methyl-4-pyridyl)methyl]isoindoline-1,3-dione

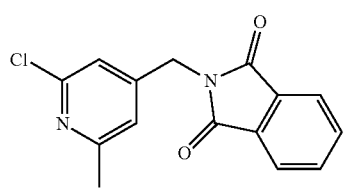 [SMILES: Cc1cc(CN2C(=O)c3ccccc3C2=O)cc(Cl)n1]

Prepare from 2-chloro-4-(chloromethyl)-6-methylpyridine (2.28 g, 12 mmol) essentially by the method described in Preparation 47 to obtain the title compound (3.67 g, 98.7% yield). $^1$H NMR (DMSO-d$_6$): δ 2.41 (s, 3H), 4.77 (s, 2H), 7.21 (s, 1H), 7.30 (s, 1H), 7.85-7.94 (m, 4H).

Preparation 53

4-[(1,3-dioxoisoindolin-2-yl)methyl]-6-methyl-pyridine-2-carbonitrile

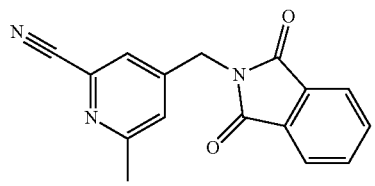 [SMILES: Cc1cc(CN2C(=O)c3ccccc3C2=O)cc(C#N)n1]

Prepare from 2-[(2-chloro-6-methyl-4-pyridyl)methyl]isoindoline-1,3-dione (3.66 g, 11.9 mmol) essentially by the method described in Preparation 48 to obtain the title compound (1.7 g, 51.5% yield). $^1$H NMR (CDCl$_3$): δ 2.58 (s, 3H), 4.84 (s, 2H), 7.36 (s, 1H), 7.51 (s, 1H), 7.75-7.81 (m, 2H), 7.88-7.93 (m, 2H).

Preparation 54

4-(aminomethyl)-6-methylpyridine-2-carbonitrile

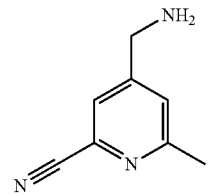

Prepare from 4-[(1,3-dioxoisoindolin-2-yl)methyl]-6-methyl-pyridine-2-carbonitrile (1.69 g, 6.1 mmol) essentially by the method described in Preparation 49 to obtain the title compound (379 mg, 41% yield). $^1$H NMR (CDCl$_3$): δ 1.47 (br s, 2H), 2.59 (s, 3H), 3.94 (s, 2H), 7.36 (s, 1H), 7.53 (s, 1H).

Preparation 55

Methyl 4-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}benzoate

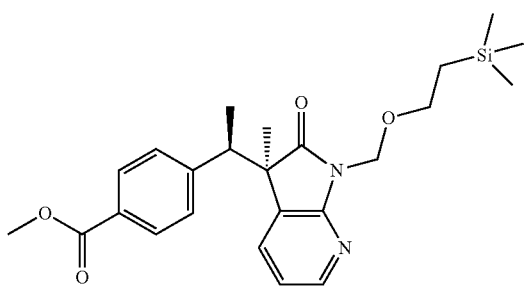

To a stirred solution of 3-methyl-1-{[2-(trimethylsilyl)ethoxy]methyl}-1,3-dihydro-2H-pyrrolo[2,3-b]pyridin-2-one (8.53 g, 30.6 mmol) and methyl 4-{(1S)-1-[(methylsulfonyl)oxy]ethyl}benzoate (8.71 g, 33.7 mmol) in DMF (153 mL) under nitrogen at 0° C. is added Cs$_2$CO$_3$ (12.0 g, 36.8 mmol). The reaction mixture is thoroughly purged with nitrogen, stirred at 0° C. for 43 hr, and gradually warmed to RT. DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a crude product as ~5:1 mixture of diastereomers. The crude product is purified by flash chromatography over silica, eluting with hexanes/EtOAc (gradient from 4:1 to 3:2). The impure chromatography fractions are concentrated under reduced pressure and repurified by flash chromatography over silica, eluting with hexanes/EtOAc (gradient from 9:1 to 3:2). All of the pure fractions from both chromatographic purifications are combined to give the title compound methyl 4-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}benzoate, isomer 1 (10.16 g, 75%), after solvent evaporation. LC/MS (m/z): 441.2 (M+H). $^1$H NMR (CDCl$_3$) δ −0.03 (s, 9H), 0.91-1.03 (m, 2H), 1.18 (d, J=7.1 Hz, 3H), 1.33 (s, 3H), 3.39 (q, J=7.1 Hz, 1H), 3.58-3.68 (m, 2H), 3.92 (s, 3H), 5.20-5.26 (m, 2H), 6.90 (dd, J=5.2, 7.3 Hz, 1H), 7.00 (dd, J=1.6, 7.3 Hz, 1H), 7.18-7.22 (m, 2H), 7.94-7.98 (m, 2H), 8.19 (dd, J=1.6, 5.2 Hz, 1H).

The minor isomer, methyl 4-{(1R)-1-[(3S)-3-methyl-2-oxo-1-{[2-(trimethylsilyl)ethoxy]methyl}-2,3-dihydro-1H-pyrrolo[2,3-b]pyridin-3-yl]ethyl}benzoate, isomer 2, was also isolated (0.80 g, 6%). LC/MS (m/z): 441.2 (M+H). $^1$H NMR (CDCl$_3$) δ −0.06 (s, 9H), 0.73-0.89 (m, 2H), 1.50 (d, J=7.2 Hz, 3H), 1.51 (s, 3H), 3.23-3.33 (m, 2H), 3.37 (q, J=7.2 Hz, 1H), 3.84 (s, 3H), 4.87-4.93 (m, 2H), 6.88-6.92 (m, 2H), 7.01 (dd, J=5.3, 7.3 Hz, 1H), 7.58 (dd, J=1.5, 7.3 Hz, 1H), 7.73-7.76 (m, 2H), 8.18 (dd, J=1.5, 5.3 Hz, 1H).

Preparation 56

Methyl 4-{(1R)-1-[(3R)-3-methyl-2-oxo-2,3-dihydro-1H-pyrrolo[2,3-b]pyridin-3-yl]ethyl}benzoate

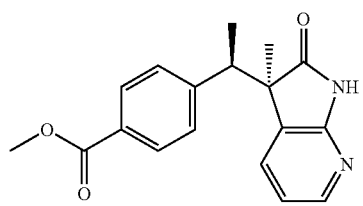 [SMILES: COC(=O)c1ccc([C@@H](C)[C@@]2(C)C(=O)Nc3ncccc32)cc1]

To a solution of methyl 4-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}benzoate, isomer 1 (10.16 g, 23.1 mmol) in DCM (154 mL) at ambient temperature is added TFA (34.9 mL, 461 mmol). After 17 hr, the solution is concentrated under reduced pressure to give a residue. To the residue is added MeOH (308 mL) and ethylenediamine (1.70 mL, 25.4 mmol). 5.0 M aqueous NaOH is added slowly at RT until the mixture reaches pH 10. After 2 hr at RT, the solution is concentrated under reduced pressure to give a residue. DCM and saturated aqueous NaHCO$_3$ are added and the layers are separated. The aqueous layer is extracted twice with DCM; the organic layers are then combined, dried over Na$_2$SO$_4$, filtered, and concentrated under reduced pressure to give the crude product. The crude product is purified by flash chromatography over silica, eluting with hexanes/EtOAc (gradient from 4:1 to 0:1). The impure chromatography fractions are concentrated under reduced pressure and repurified by flash chromatography over silica, eluting with hexanes/EtOAc (gradient from 4:1 to 0:1). All of the pure fractions from both chromatographic purifications are combined to give the title compound (5.11 g, 71%), after solvent evaporation. LC/MS (m/z): 311.0 (M+H). The material is analyzed by chiral chromatography (Column: Chiralpak AD-H 4.6×150 mm; eluent: 90:10, EtOH:ACN (containing 0.2% IPAm); flow: 1.0 mL/min at UV 225 nm) to show that it is >99% ee and corresponds to the second eluting isomer with t$_R$=5.42 min.

Preparation 57

4-{(1R)-1-[(3R)-3-methyl-2-oxo-2,3-dihydro-1H-pyrrolo[2,3-b]pyridin-3-yl]ethyl}benzoic acid

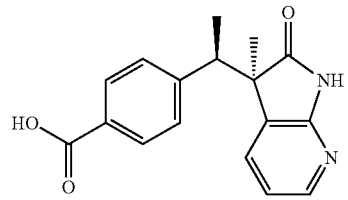 [SMILES: C[C@H](c1ccc(C(=O)O)cc1)[C@@]1(C)C(=O)Nc2ncccc21]

To a solution of methyl 4-{(1R)-1-[(3R)-3-methyl-2-oxo-2,3-dihydro-1H-pyrrolo[2,3-b]pyridin-3-yl]ethyl}benzoate (3.92 g, 12.6 mmol) in THF (63.1 mL) at ambient temperature was added a solution of LiOH (907 mg, 37.9 mmol) in water (12.6 mL). After 20 hr, the reaction mixture is diluted with DCM and saturated aqueous NaCl. 1.0 M HCl is added slowly at RT until the mixture reaches pH ~2. The layers are separated, and the aqueous layer is extracted three times with CHCl$_3$/2-propanol (3:1). The organic layers are combined, dried over Na$_2$SO$_4$, filtered, and concentrated under reduced pressure to give the title compound (3.73 g, 100%). LC/MS (m/z): 297.0 (M+H).

Example 1

First Procedure

N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide

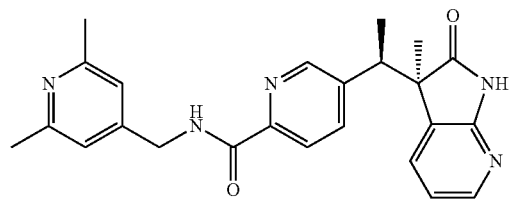 [SMILES: Cc1cc(CNC(=O)c2ccc([C@@H](C)[C@@]3(C)C(=O)Nc4ncccc43)cn2)cc(C)n1]

Scheme 3, Step E: To a solution of 5-{(1R)-1-[(3R)-3-methyl-2-oxo-2,3-dihydro-1H-pyrrolo[2,3-b]pyridin-3-yl]ethyl} pyridine-2-carboxylic acid (100 mg, 0.34 mmol) and TEA (0.23 mL, 1.68 mmol) in DMF (2.0 mL) at RT is added 1-(2,6-dimethylpyridin-4-yl)methanamine dihydrochloride (105 mg, 0.504 mmol) and 2,4,6-tripropyl-1,3,5,2,4,6-trioxatriphosphorinane-2,4,6-trioxide (50% by weight in EtOAc, 0.343 mL, 0.57 mmol). After 17 hr, DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a residue. The residue is purified by flash chromatography over silica, eluting with DCM/MeOH (gradient from 1:0 to 9:1) to give the title compound (107 mg, 75% yield), after solvent evaporation. LC-ES/MS (m/z): 416.2 (M+H). The material is analyzed by chiral SFC (Column: CHIRALPAK® AD-H; eluent: 40:60, EtOH (containing 0.2% IPAm):CO$_2$; flow: 5 mL/min at UV 225 nm) indicating 97.4% ee and corresponding to the second eluting isomer with $t_R$=2.95 min. $[\alpha]_D^{20}$= −79.32° (c=1.0, CHCl$_3$).

Example 1

Second Procedure

N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide To a solution of N-[(2,6-dimethylpyridin-4-yl)methyl]-5-{(1R)-1-[(3R)-3-methyl-2-oxo-1-{[2-(trimethylsilyl)ethoxy]methyl}-2,3-dihydro-1H-pyrrolo[2,3-b]pyridin-3-yl]ethyl}pyridine-2-carboxamide (15.4 g, 28.2 mmol) in DCM (308 mL) at RT is added TFA (154 mL, 2.04 mol) in portions. The reaction mixture is stirred at RT for 1.5 hr, concentrated under reduced pressure, and dried under vacuum to give a residue. The residue is dissolved in THF (308 mL) and NH$_4$OH (30% NH$_3$ in water, 154 mL) is added in portions causing the temperature to rise to 45° C. The reaction mixture is cooled to RT, stirred for 40 min, and diluted with DCM and water. The layers are separated and the aqueous layer is extracted with DCM. The organic layers are combined and washed with saturated aqueous NaCl. The aqueous layer is extracted again with DCM. The organic layers are combined, dried over Na$_2$SO$_4$, filtered, and concentrated under reduced pressure to give a residue. The residue is purified by flash chromatography over silica, eluting with DCM/EtOAc/MeOH (gradient from 50:50:0 to 47.5:47.5:5) to give a solid. The solid is dried for 1 day in a vacuum oven. The solid is dissolved in MTBE (600 mL) and EtOAc (100 mL) and washed twice with water. The aqueous layer is extracted with EtOAc. The organic layers are combined, dried over Na$_2$SO$_4$, filtered, and concentrated under reduced pressure to give a solid. The solid is dried for 3 days under a stream of nitrogen and for 1 day in a vacuum oven. The material is dissolved in 50 mL of 4:1 EtOH:H$_2$O, and concentrated under reduced pressure. The dissolution/concentration procedure is repeated twice to give a solid. The solid is dried for about 20 hr in a vacuum oven to give the title compound (5.9 g, 50% yield). The material is analyzed by chiral SFC (Column: CHIRALPAK® AD-H; eluent: 40:60, EtOH (containing 0.2% IPAm):CO$_2$; flow: 5 mL/min at UV 225 nm) indicating 97.4% ee and corresponding to the second eluting isomer with $t_R$=2.97 min. LC-ES/MS (m/z): 416.2 (M+H).

Example 1

Third Procedure

N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide Scheme 5, steps D and E: The following may be run in two batches and the two batches combined before chromatography: (3R)-3-[(1R)-1-(6-bromo-3-pyridyl)ethyl]-3-methyl-1H-pyrrolo[2,3-b]pyridin-2-one (72.4 g, 217.94 mmol) is added to a 2 L Parr autoclave, equipped with a mechanical stirrer, containing anhydrous toluene (925 mL), phenol (22.7 g, 241.2 mmol), and TEA (115.0 g, 1136.4 mmol). The autoclave is sealed, thoroughly purged with N$_2$, and Pd(OAc)$_2$ (500 mg, 2.2 mmol) followed by 4,5-bis(diphenylphosphino)-9,9-dimethylxanthene (1.3 g, 2.2 mmol) are added. The autoclave mixture is again purged with N$_2$ followed by CO, pressurized to 60 psi with CO, and heated to 85° C. overnight. The reaction mixture is cooled slightly, opened, and (2,6-dimethyl-4-pyridyl)methanamine dihydrochloride (50.1 g, 239.6 mmol) is added quickly. The autoclave is resealed and heated at 120° C. for 1 hr. The reaction mixture is cooled to RT, diluted with EtOAc (~1 L), filtered over a bed of diatomaceous earth, and the filtrate is concentrated under reduced pressure. The residue is purified by flash chromatography over silica, eluting with acetone in hexanes (gradient from 4:1 to 1:0), to give crude title compound, after solvent evaporation, as a pale yellow solid. This material is dissolved in EtOAc (1 L), SILIABOND® Metal Scavenger (200 g, SILICYCLE®) is added, and the resulting mixture is stirred at RT overnight. The mixture is filtered over a bed of diatomaceous earth, washed with EtOAc (~2 L), and the filtrate is concentrated under reduced pressure to obtain the title compound (181.3 g, 77.2% yield, combination of 2 runs) as a white solid. The material is analyzed by chiral SFC (Column: CHIRALPAK® AD-H; eluent: 40:60, EtOH (containing 0.2% IPAm):CO$_2$; flow: 5 mL/min at UV 225 nm), $t_R$=2.95 min, indicating >98% ee. LC-ES/MS (m/z): 416.2 (M+H).

Example 1A

Hydrated N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide hydrochloride N-[(2,6-Dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide (8 g, 19.3 mmol) is dissolved in 100 mL of acetone to a yellow solution at 1000 rpm/60° C. A solution of 1 M HCl in EtOAc (40 mL, 40.08 mmol) is added, and a white gum precipitates out of solution quickly. The sample is stirred at 60° C. for 30 min, whereupon a slurry of white solid begins to form in the solution. After the full slurry time, the sample is a thick layer of white solid under light yellow solution. The white solid is isolated by vacuum filtration, dried on filter paper for 15 min, and then further dried in a vacuum oven for 1 hr at 70° C., to obtain the title product as a white crystalline solid in hydrated form (5.69 g, 65.4% yield).

A prepared sample of the crystalline hydrated HCl salt is characterized by an XRD pattern using CuKa radiation as having diffraction peaks (2-theta values) as described in Table 1 below, and in particular having peaks at 20.70 in combination with one or more of the peaks selected from the group consisting of 19.8°, 12.9°, and 14.0°; with a tolerance for the diffraction angles of 0.2 degrees.

TABLE 1

X-ray powder diffraction peaks of Example 1A, Hydrated N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide hydrochloride

| Peak | Angle (°2-Theta) +/− 0.2° | Relative Intensity (% of most intense peak) |
|---|---|---|
| 1 | 12.9 | 47.1% |
| 2 | 14.0 | 46.0% |
| 3 | 16.1 | 30.8% |
| 4 | 19.8 | 50.0% |
| 5 | 20.7 | 100.0% |
| 6 | 22.1 | 32.2% |
| 7 | 23.3 | 23.8% |
| 8 | 24.7 | 42.4% |
| 9 | 26.0 | 16.1% |
| 10 | 28.2 | 17.6% |

Example 1B

Methanolated N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide hydrochloride N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide (366.0 mg, 0.88 mmol) is dissolved in 2 mL of EtOAc to a yellow solution at 1000 rpm/60° C. 1 M HCl in EtOAc (1.25 mL, 1.84 mmol) is added, and a white solid precipitates out of solution instantly. The mixture is slurried for 30 min at 60° C., whereupon the solid converts to a bright white granular birefringent solid. The sample is cooled to 5° C. to give an off-white solid that is isolated by vacuum filtration. This cake of solid is then rinsed with another 500 µL of EtOAc and the solid becomes a slightly brighter white. This cake is dried on the filter paper for 15 min, and is then dissolved in 1 mL of MeOH at 60° C. The sample is removed to the benchtop to cool then refrigerated for 2 hr at 5° C. to yield the crystalline methanolate of the HCl salt upon collection by vacuum filtration.

A prepared sample of the crystalline methanolate of the HCl salt is characterized by an XRD pattern using CuKa radiation as having diffraction peaks (2-theta values) as described in Table 2 below, and in particular having peaks at 16.30 in combination with one or more of the peaks selected from the group consisting of 24.6°, 20.8°, and 20.1°; with a tolerance for the diffraction angles of 0.2 degrees.

TABLE 2

X-ray powder diffraction peaks of Example 1B, methanolated N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide hydrochloride

| Peak | Angle (°2-Theta) +/− 0.2° | Relative Intensity (% of most intense peak) |
|---|---|---|
| 1 | 12.5 | 8.7% |
| 2 | 14.4 | 2.9% |
| 3 | 15.5 | 2.4% |
| 4 | 16.3 | 100.0% |

TABLE 2-continued

X-ray powder diffraction peaks of Example 1B, methanolated N-[(2,6-dimethylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide hydrochloride

| Peak | Angle (°2-Theta) +/− 0.2° | Relative Intensity (% of most intense peak) |
|---|---|---|
| 5 | 20.1 | 14.1% |
| 6 | 20.8 | 35.5% |
| 7 | 22.4 | 4.6% |
| 8 | 24.6 | 58.5% |
| 9 | 25.6 | 3.9% |
| 10 | 30.3 | 1.9% |

Example 2

N-[(2,6-dimethyl-4-pyridyl)methyl]-4-[(1R)-1-[(3R)-3-methyl-2-oxo-1H-pyrrolo[2,3-b]pyridin-3-yl]ethyl]benzamide

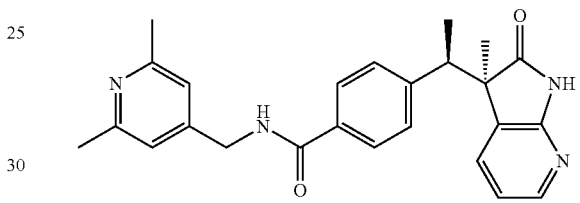

Scheme 9, step A (Q=CH, X=CH, Y=CH, Z=N, R=Me): To a solution of 4-[(1R)-1-[(3R)-3-methyl-2-oxo-1H-pyrrolo[2,3-b]pyridin-3-yl]ethyl]benzoic acid (0.5 g, 1.503 mmol) and (2,6-dimethyl-4-pyridyl)methanamine hydrochloride (426 mg, 3.0 mmol) in DMF (4 mL) is added TEA (628 µL, 3.0 mmol) and T3P (50% by weight in EtOAc, 1.8 mL, 3.0 mmol) and the resulting mixture is stirred at RT overnight. The reaction mixture is diluted with saturated aqueous NaCl and extracted with EtOAc. The organic layer is separated, dried over Na₂SO₄, filtered, concentrated under reduced pressure, and purified by flash chromatography over silica, eluting with a gradient of 0-7% MeOH in DCM, to give the title compound (548 mg, 88% yield) after solvent evaporation. LC-ES/MS (m/z): 415.2 (M+H).

Example 3

N-[(2-ethyl-6-methylpyridin-4-yl)methyl]-4-{(1R)-1-[(3R)-3-methyl-2-oxo-2,3-dihydro-1H-pyrrolo[2,3-b]pyridin-3-yl]ethyl}benzamide

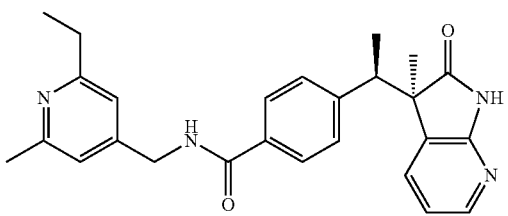

Scheme 9, step A (Q=CH, X=CH, Y=CH, Z=N, R=Et): To a solution 4-{(1R)-1-[(3R)-3-methyl-2-oxo-2,3-dihydro- 1H-pyrrolo[2,3-b]pyridin-3-yl]ethyl}benzoic acid (45 mg, 0.15 mmol) in DMF (0.76 mL) is added 1-(2-ethyl-6-methylpyridin-4-yl) methanamine dihydrochloride (51 mg, 0.23 mmol), DIPEA (0.15 mL, 0.91 mmol), and HATU (70 mg, 0.18 mmol) at RT. After 17 hr, the reaction mixture is purified by reverse phase chromatography (Phenomenex Gemini-NX C18 column) eluting with 10 mmol ammonium bicarbonate (pH 10 with 5% methanol) and ACN to give the title compound (53.7 mg, 83% yield), after solvent evaporation. LC-ES/MS (m/z): 429.2 (M+H).

Example 4

N-[(2-cyclopropyl-6-methyl-4-pyridyl)methyl]-4-[(1R)-1-[(3R)-3-methyl-2-oxo-1H-pyrrolo[2,3-b]pyridin-3-yl]ethyl]benzamide

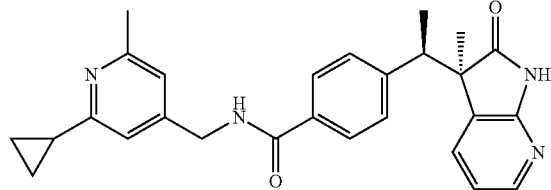 [SMILES: Cc1cc(CNC(=O)c2ccc([C@@H](C)[C@@]3(C)C(=O)Nc4ncccc43)cc2)cc(C2CC2)n1]

Scheme 9, step A (R=CH, X=CH, Y=CH, Z=N, R=c-Pr): Prepare from 4-{(1R)-1-[(3R)-3-methyl-2-oxo-2,3-dihydro-1H-pyrrolo[2,3-b]pyridin-3-yl]ethyl}benzoic acid (50 mg, 0.17 mmol) and (2-cyclopropyl-6-methyl-4-pyridyl)methanamine dihydrochloride (48 mg, 0.2 mmol) essentially by the method described in Example 1:First Procedure, to obtain the title compound (73 mg, 98% yield). LC-ES/MS (m/z): 441.2 (M+H).

Example 5

N-[(2-cyclobutyl-6-methylpyridin-4-yl)methyl]-4-{(1R)-1-[(3R)-3-methyl-2-oxo-2,3-dihydro-1H-pyrrolo[2,3-b]pyridin-3-yl]ethyl}benzamide

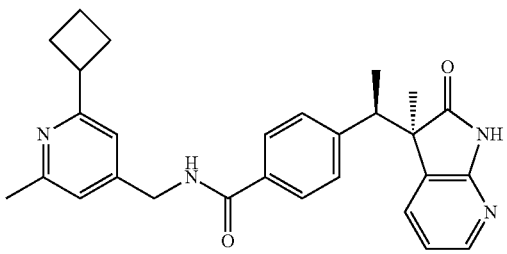 [SMILES: Cc1cc(CNC(=O)c2ccc([C@@H](C)[C@@]3(C)C(=O)Nc4ncccc43)cc2)cc(C2CCC2)n1]

Scheme 9, step A (Q=CH, X=CH, Y=CH, Z=N, R=c-Bu): Prepare from 4-{(1R)-1-[(3R)-3-methyl-2-oxo-2,3-dihydro-1H-pyrrolo[2,3-b]pyridin-3-yl]ethyl}benzoic acid (45 mg, 0.15 mmol) and (2-cyclobutyl-6-methyl-4-pyridyl)methanamine dihydrochloride (57 mg, 0.23 mmol) essentially by the method described in Example 3, to give the title compound (58.5 mg, 85% yield). LC-ES/MS (m/z): 455.2 (M+H).

Example 6

N-[(2-cyclopentyl-6-methylpyridin-4-yl)methyl]-4-{(1R)-1-[(3R)-3-methyl-2-oxo-2,3-dihydro-1H-pyrrolo[2,3-b]pyridin-3-yl]ethyl}benzamide

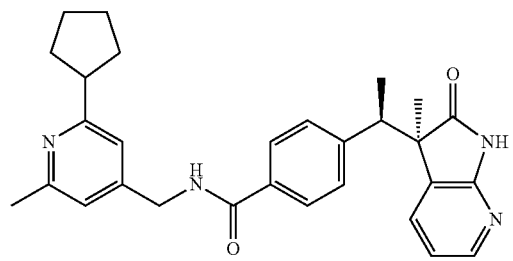 [SMILES: Cc1cc(CNC(=O)c2ccc([C@@H](C)[C@@]3(C)C(=O)Nc4ncccc43)cc2)cc(C2CCCC2)n1]

Scheme 9, step A (Q=CH, X=CH, Y=CH, Z=N, R=c-pentyl): Prepare from 4-{(1R)-1-[(3R)-3-methyl-2-oxo-2,3-dihydro-1H-pyrrolo[2,3-b]pyridin-3-yl]ethyl}benzoic acid (45 mg, 0.15 mmol) and (2-cyclopentyl-6-methyl-4-pyridyl)methanamine dihydrochloride (60 mg, 0.23 mmol) essentially by the method described in Example 3, to give the title compound (65.1 mg, 92% yield). LC-ES/MS (m/z): 469.2 (M+H).

Example 7

N-[(4,6-dimethylpyridin-2-yl)methyl]-4-{(1R)-1-[(5R)-5-methyl-6-oxo-6,7-dihydro-5H-pyrrolo[2,3-d]pyrimidin-5-yl]ethyl}benzamide

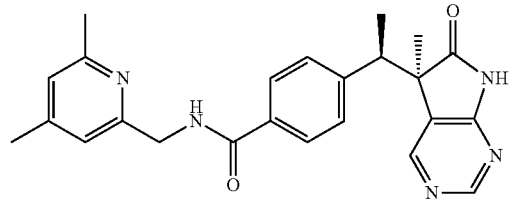 [SMILES: Cc1cc(C)nc(CNC(=O)c2ccc([C@@H](C)[C@@]3(C)C(=O)Nc4ncncc43)cc2)c1]

Scheme 9, Step A (Q=N, X=CH, Y=N, Z=CH, R=Me): To a solution of 4-{(1R)-1-[(5R)-5-methyl-6-oxo-6,7-dihydro-5H-pyrrolo[2,3-d]pyrimidin-5-yl]ethyl}benzoic acid (300 mg, 1.01 mmol) and TEA (0.422 mL, 3.03 mmol) in DMF (6.0 mL) at RT is added 1-(4,6-dimethylpyridin-2-yl) methanamine (Aldrich, CAS#76457-15-3, 206 mg, 1.51 mmol) and 2,4,6-tripropyl-1,3,5,2,4,6-trioxatriphosphorinane-2,4,6-trioxide (50% by weight in EtOAc, 1.03 mL, 1.72 mmol). After 3 hr, DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a residue. The crude product is purified by flash chromatography over silica, eluting with DCM/MeOH (gradient from 1:0 to 9:1) to give the title compound (312 mg, 74% yield), after solvent evaporation. LC-ES/MS (m/z): 416.2 (M+H).

Example 8

N-[(4,6-dimethylpyridin-2-yl)methyl]-4-{(1R)-1-[(5R)-5-methyl-6-oxo-6,7-dihydro-5H-pyrrolo[2,3-d]pyrimidin-5-yl]ethyl}benzamide

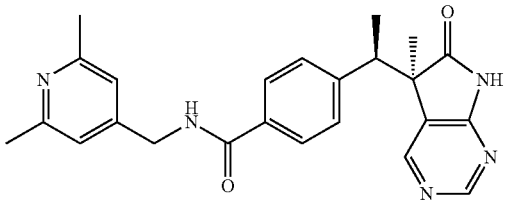 [SMILES: Cc1cc(CNC(=O)c2ccc([C@@H](C)[C@@]3(C)C(=O)Nc4ncncc43)cc2)cc(C)n1]

Scheme 9, Step A (Q=N, X=CH, Y=CH, Z=N, R=Me): To a solution of 4-{(1R)-1-[(5R)-5-methyl-6-oxo-6,7-dihydro-5H-pyrrolo[2,3-d]pyrimidin-5-yl]ethyl}benzoic acid (316 mg, 1.06 mmol) and TEA (0.44 mL, 3.19 mmol) in DMF (6.3 mL) at RT is added 1-(2,6-dimethylpyridin-4-yl)methanamine (188 mg, 1.38 mmol) and 2,4,6-tripropyl-1,3,5,2,4,6-trioxatriphosphorinane-2,4,6-trioxide (50% by weight in EtOAc, 1.08 mL, 1.81 mmol). After 4 hr, DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a residue. The crude product is purified by flash chromatography over silica, eluting with DCM/MeOH (gradient from 1:0 to 9:1) to give the title compound (323 mg, 73% yield), after solvent evaporation. LC-ES/MS (m/z): 416.2 (M+H).

Example 9

N-[(2-cyclopropyl-6-methylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide

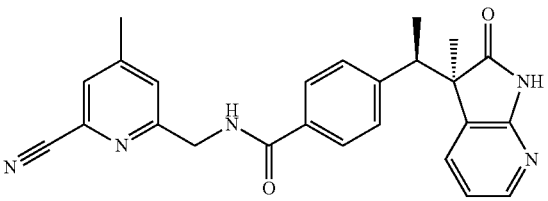 [SMILES: Cc1cc(C#N)nc(CNC(=O)c2ccc([C@@H](C)[C@@]3(C)C(=O)Nc4ncccc43)cc2)c1]

Scheme 9, Step A (Q=CH, X=N, Y=CH, Z=N, R-c-Pr): To a solution of 5-{(1R)-1-[(3R)-3-methyl-2-oxo-2,3-dihydro-1H-pyrrolo[2,3-b]pyridin-3-yl]ethyl} pyridine-2-carboxylic acid (75 mg, 0.25 mmol) and TEA (0.176 mL, 1.26 mmol) in DMF (1.5 mL) at RT is added 1-(2-cyclopropyl-6-methylpyridin-4-yl)methanamine dihydrochloride (89 mg, 0.38 mmol) and 2,4,6-tripropyl-1,3,5,2,4,6-trioxatriphosphorinane-2,4,6-trioxide (50% by weight in EtOAc, 0.257 mL, 0.428 mmol). After 17 hr, DCM and saturated aqueous NaHCO$_3$ are added and the layers are separated. The aqueous layer is extracted twice with DCM. The organic layers are combined, dried over Na$_2$SO$_4$, filtered, and concentrated under reduced pressure to give a residue. The crude product is purified by flash chromatography over silica, eluting with DCM/MeOH (gradient from 1:0 to 9:1) to give the title compound (75 mg, 67%), after solvent evaporation. LC-ES/MS (m/z): 442.2 (M+H).

Example 10

N-[(2,6-dimethyl-4-pyridyl)methyl]-5-[(1R)-1-[(5R)-5-methyl-6-oxo-7H-pyrrolo[2,3-d]pyrimidin-5-yl]ethyl]pyridine-2-carboxamide

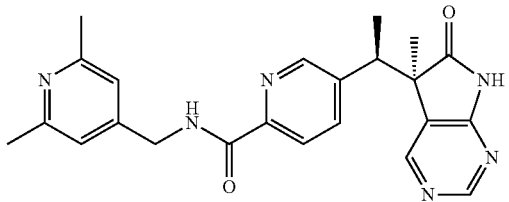

Scheme 9, step A (Q=N, X=N, Y=CH, Z=N, R=Me): Prepare from 5-[(1R)-1-[(5R)-5-methyl-6-oxo-7H-pyrrolo[2,3-d]pyrimidin-5-yl]ethyl]pyridine-2-carboxylic acid (100 mg, 0.334 mmol) and (2,6-dimethyl-4-pyridyl)methanamine hydrochloride (1.5 equiv., 0.51 mmol) essentially by the method described in Example 3 to give the title compound (87 mg, 62% yield). LC-ES/MS (m/z): 417.2 (M+H).

Example 11

N-[(6-cyano-4-methyl-2-pyridyl)methyl]-4-[(1R)-1-[(3R)-3-methyl-2-oxo-1H-pyrrolo[2,3-b]pyridin-3-yl]ethyl]benzamide

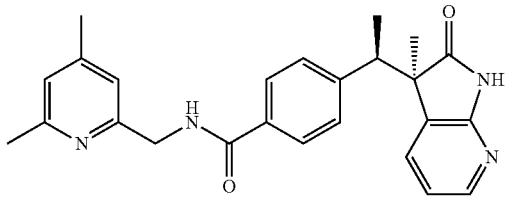 [SMILES: Cc1cc(C)nc(CNC(=O)c2ccc([C@@H](C)[C@@]3(C)C(=O)Nc4ncccc43)cc2)c1]

Scheme 9, step A (Q=CH, X=CH, Y=N, Z=CH, R=CN): Prepare from 4-{(1R)-1-[(3R)-3-methyl-2-oxo-2,3-dihydro-1H-pyrrolo[2,3-b]pyridin-3-yl]ethyl}benzoic acid (0.05 g, 0.17 mmol) and 6-(aminomethyl)-4-methyl-pyridine-2-carbonitrile (0.03 g, 0.2 mmol) essentially by the method described in Example 1:First Procedure to give the title compound (49 mg, 68% yield). LC-ES/MS (m/z): 426.2 (M+H).

Example 12

N-[(4,6-dimethylpyridin-2-yl)methyl]-4-{(1R)-1-[(3R)-3-methyl-2-oxo-2,3-dihydro-1H-pyrrolo[2,3-]pyridin-3-yl]ethyl}benzamide Scheme 9, step A (Q=CH, X=CH, Y=N, Z=CH, R=Me): Prepare from 4-{(1R)-1-[(3R)-3-methyl-2-oxo-2,3- dihydro-1H-pyrrolo[2,3-b]pyridin-3-yl]ethyl}benzoic acid (350 mg, 1.2 mmol) and (4,6-dimethyl-2-pyridyl)methanamine (173 mg, 1.3 mmol) essentially by the method described in Example 3 to obtain the title compound (192 mg, 39% yield). LC-ES/MS (m/z): 415.2 (M+H).

Example 13

N-[(2-ethyl-6-methylpyridin-4-yl)methyl]-5-{(1R)-1-[(3R)-3-methyl-2-oxo-2,3-dihydro-1H-pyrrolo[2,3-b]pyridin-3-yl]ethyl}pyridine-2-carboxamide

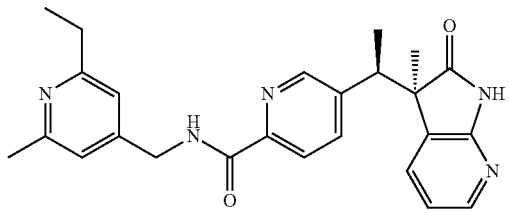 [SMILES: CCc1cc(CNC(=O)c2ccc([C@@H](C)[C@@]3(C)C(=O)Nc4ncccc43)cn2)cc(C)n1]

Scheme 9, step A (Q=CH, X=N, Y=CH, Z=N, R=Et): Prepare from 5-[(1R)-1-[(3R)-3-methyl-2-oxo-1H-pyrrolo[2,3-b]pyridin-3-yl]ethyl]pyridine-2-carboxylic acid (45 mg, 0.15 mmol) and (2-ethyl-6-methyl-4-pyridyl)methanamine dihydrochloride (50 mg, 0.23 mmol) essentially by the method described in Example 3 to obtain the title compound (51.2 mg, 79% yield). LC-ES/MS (m/z): 430.3 (M+H).

Example 14

4-{(1R)-1-[(3R)-3-methyl-2-oxo-2,3-dihydro-1H-pyrrolo[2,3-b]pyridin-3-yl]ethyl}-N-{[2-methyl-6-(propan-2-yl)pyridin-4-yl]methyl}benzamide

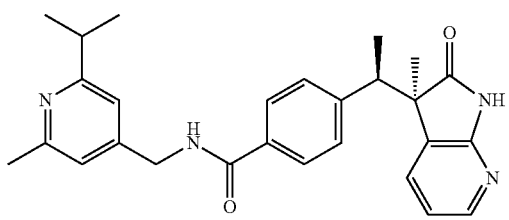 [SMILES: Cc1cc(CNC(=O)c2ccc([C@@H](C)[C@@]3(C)C(=O)Nc4ncccc43)cc2)cc(C(C)C)n1]

Scheme 9, step A (Q=CH, X=CH, Y=CH, Z=N, R=i-Pr): Prepare from 4-[(1R)-1-[(3R)-3-methyl-2-oxo-1H-pyrrolo[2,3-b]pyridin-3-yl]ethyl]benzoic acid (45 mg, 0.15 mmol) and (2-isopropyl-6-methyl-4-pyridyl)methanamine (37 mg, 0.23 mmol) essentially by the method described in Example 3 to obtain the title compound (57.5 mg, 86% yield). LC-ES/MS (m/z): 443.3 (M+H).

Example 15

N-[(4,6-dimethylpyridin-2-yl)methyl]-5-{(1R)-1-[(3R)-3-methyl-2-oxo-2,3-dihydro-1H-pyrrolo[2,3-b]pyridin-3-yl]ethyl}pyridine-2-carboxamide

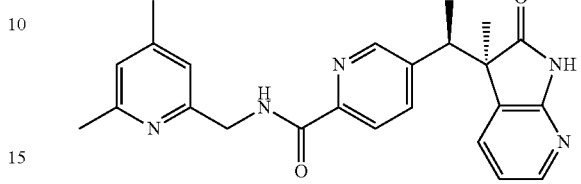

Scheme 9, step A (Q=CH, X=N, Y=N, Z=CH, R=Me): Prepare from 5-[(1R)-1-[(3R)-3-methyl-2-oxo-1H-pyrrolo[2,3-b]pyridin-3-yl]ethyl]pyridine-2-carboxylic acid (45 mg, 0.15 mmol) and (4,6-dimethyl-2-pyridyl)methanamine dihydrochloride (47 mg, 0.23 mmol) essentially by the method described in Example 3 to obtain the title compound (57.5 mg, 86% yield). LC-ES/MS (m/z): 416.3 (M+H).

Example 16

N-[(2-cyano-6-methylpyridin-4-yl)methyl]-4-{(1R)-1-[(3R)-3-methyl-2-oxo-2,3-dihydro-1H-pyrrolo[2,3-b]pyridin-3-yl]ethyl}benzamide

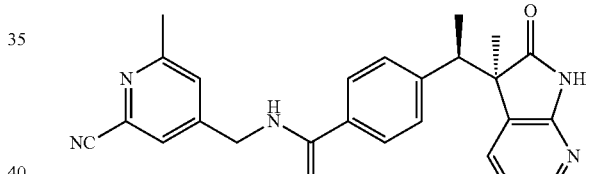

Scheme 9, step A (Q=CH, X=CH, Y=CH, Z=N, R=CN): Prepare from 4-[(1R)-1-[(3R)-3-methyl-2-oxo-1H-pyrrolo[2,3-b]pyridin-3-yl]ethyl]benzoic acid (45 mg, 0.15 mmol) and 4-(aminomethyl)-6-methyl-pyridine-2-carbonitrile (70 mg, 0.18 mmol) essentially by the method described in Example 3 to obtain the title compound (50 mg, 77% yield). LC-ES/MS (m/z): 426.3 (M+H).

Inhibition of cAMP Production by CGRP Receptor Antagonists

The hCGRP (human calcitonin gene-related peptide) receptor is functionally coupled to the Gαs proteins. Stimulation of hCGRP results in an increased synthesis of intracellular cAMP and can be blocked by the addition of receptor antagonists. Receptor activity is thus a reflection of the amount of cAMP present within cells which can be detected using standard in vitro technology.

Cell Culture:

Cultured SK-N-MC neuroblastoma cells (ATCC® HTB-10™) that endogenously express the hCGRP receptor are grown in Eagle's Minimum essential medium (HYCLONE™) supplemented with 10% heat-inactivated Fetal bovine serum (FBS; GIBCO®), Non-Essential Amino Acids (GIBCO®), 1 mM sodium pyruvate, 2 mM L-glutamine, 100 U/mL of penicillin, and 10 μg/mL of streptomycin to about 70% confluency. After providing fresh medium, the cells are incubated at 37° C. overnight. On the day of the assay, cells are detached using ACCUTASE® (MP Biomedicals), resuspended in assay buffer [Hank's Balanced Salt Solution/Dulbecco's phosphate-buffered saline with 100 mg/mL each of $CaCl_2$ and $MgCl_2$ mixed 1:2, 3.3 mM 4-(2-hydroxyethyl)-1-piperazineethanesulfonic acid, 0.03% bovine serum albumin, and 0.5 mM 1-methyl-3-isobutylxanthine (as inhibitor of cAMP)], and seeded 3-5K/well into 384-well, poly-D-lysine coated white plates (BD Biosciences).

Inhibition of cAMP Production:

For dose-response studies, compounds are serially diluted 1:3 in dimethyl sulfoxide and then 1:10 into assay buffer. Human CGRP (0.8 nM; Bachem) as a receptor-specific agonist for the hCGRP receptor is mixed with diluted compound and added to the cells as the challenge stimulant at their $EC_{80}$ concentrations.

Data Analysis:

The amount of intracellular cAMP is quantitated using HTRF technology (Cisbio) as per vendor instructions. Briefly, cAMP-d2 conjugate and anti-cAMP-cryptate conjugate in lysis buffer are incubated with the treated cells at room temperature for 90 min. The HTRF signal is immediately detected using an ENVISION® plate reader (Perkin-Elmer) to calculate the ratio of fluorescence at 665 to 620 nM. The raw data are converted to cAMP amount (pmole/well) using a cAMP standard curve generated for each experiment. Relative $EC_{50}$ values are calculated from the top-bottom range of the concentration response curve using a four-parameter logistic curve fitting program (ACTIVITYBASE® v5.3.1.22 or GENEDATA SCREENER® v12.0.4), and $K_b$ values are estimated as agonist-corrected $IC_{50}$ values using the equation:

$$K_b = (IC_{50})/[1+([Agonist]/EC_{50})].$$

Estimated $K_b$ values are reported as mean values±SEM, averaged from the number of runs (n).

Following the procedure essentially as described above, the compounds of Examples 1-16 have $K_b$ measured at human CGRP receptor shown in Table 3. This demonstrates that the compounds of Examples 1-16 are antagonists of human CGRP receptor in vitro.

TABLE 3

Measured Kb at human CGRP receptor in vitro

| Example No. | Kb hCGRP (nM) | N (number of runs) |
| --- | --- | --- |
| 1 | 0.0465 ± 0.0097 | 8 |
| 2 | 0.0366 ± 0.0154 | 6 |
| 3 | 0.0173 | 1 |
| 4 | 0.0266 | 1 |
| 5 | 0.00696 | 1 |
| 6 | 0.0182 | 1 |
| 7 | 0.0977 ± 0.00276 | 2 |
| 8 | 0.0472 ± 0.00564 | 3 |
| 9 | 0.0245 | 1 |
| 10 | 0.198 ± 0.0459 | 2 |
| 11 | 0.0404 | 1 |
| 12 | 0.0428 ± 0.0130 | 2 |
| 13 | 0.0453 ± 0.00153 | 2 |
| 14 | 0.0260 | 1 |
| 15 | 0.171 ± 0.0339 | 3 |
| 16 | 0.813 | 1 |

CGRP (Calcitonin Gene-Related Peptide) Non-Human Primates Studies

Capsaicin-induced dermal blood flow (DBF) is used as a target engagement biomarker to assess CGRP receptor activity in nonhuman primates (NHPs). Methods are adapted from earlier published procedures [Hershey et al., *Regulatory Peptides*, Volume 127, Issue 1-3, pp. 71-77, 2005].

Study Population:

Animal studies may be performed under protocols approved by the Covance Institutional Animal Care and Use Committee. Cynomolgus NHPs may be used given the close homology between NHP and human CGRP receptor. The study population may include healthy, CGRP antagonist naive cynomolgus NHP males weighing ~3-4 kg.

Cynomolgus NHPs are enrolled in the study based on prescreening for capsaicin responsiveness. NHPs that exhibited ≥50% increase in blood flow over baseline with 2 mg (20 μL/ring) topical capsaicin treatment (average of 3 O-rings) over baseline in response to capsaicin in the screened arm and stable physiology during the imaging period are included in a study with the compound of Example 1. NHPs are used in a cross over design in which all NHPs received all doses after a two week wash-out period. Total n=10 NHPs per group.

Dose Administration:

NHPs each receive vehicle, 3, 10 and 30 mg/kg of the CGRP receptor antagonist Example 1 administered orally (10% Acacia w/v/0.05% Antifoam 1510-US emulsion v/v/in purified water) 90 min prior to the capsaicin administration in the laser Doppler imaging (LDI) experiment.

Pharmacodynamic Sampling:

Animals are fasted overnight prior to each capsaicin challenge. On the day of the experiment, the NHPs are anesthetized with 1% Isoflurane for approximately 30 min prior to scanning. The NHPs are placed in a quiet, temperature-controlled room supine on a warm small surgical blanket and the shaved arm is placed on a heating pad under the laser head. Three neoprene O-rings (size=8 mm ID) are placed on the NHP forearm, approximately 1 cm apart. During a 30-minute stabilization period, preliminary scans are obtained to confirm correct positioning of the O-rings. Once baseline temperature (approximately 37° C.) is stabilized, a baseline scan is collected. After the baseline scan is completed, 20 μl of capsaicin solution (50 mg of capsaicin in a solution of 170 μl EtOH, 80 μl TWEEN® 20, 250 μl purified $H_2O$) is applied to each O-ring. Scanning is continued every 5 min for an additional 25 min (85, 90, 95, 100, 105, 110, 115, and 120 min post-treatment with CGRP antagonist compound).

Analysis and Statistics:

LDI repeat scans are analyzed using Moor software v.5.3 (Moor Instruments, Wilmington, Del.) by region of interest signal analysis, and Microsoft Excel worksheets are used for averaging the signal from the regions of interest at a given time point. Changes in DBF are reported as percent change from baseline DBF. [Two LDI data points were removed from the analysis due to statistically low exposure of the compound of example 1 (standardized residual method with 95% threshold)]. Analyzed data is entered into Graphpad PRISM® 4.0 for graphing and a repeated measurement mixed-effect model in SAS® 9.1 is used for statistical analysis. Data is expressed as mean+/−SEM.

Using a mixed effect model with repeated measurement (autoregressive correlation via AR1 process) and false discovery rate multiple adjustments, compared to vehicle, the compound of Example 1 at 3 mg/kg 10 mg/kg and 30 mg/kg gives statistically significant decreased blood flow increase following a capsaicin challenge with group mean inhibition of 32.1% ($p<0.008$), 46.1% ($p<0.0004$) and 58.8% ($p<0.00002$) respectively, providing evidence of CGRP target engagement.

We claim:

1. A compound of the formula:

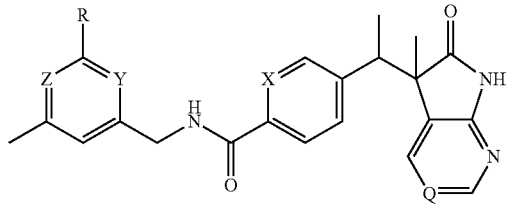

wherein

Y is CH or N

Z is CH or N;

provided that when Y is CH, Z is N and when Y is N, Z is CH;

X is CH or N;

Q is CH or N; and

R is C1-C3 alkyl, C3-C5 cycloalkyl, or CN;

or a pharmaceutically acceptable salt thereof.

2. The compound or salt according to claim 1 wherein Q is CH.

3. The compound or salt according to claim 2 wherein Y is CH and Z is N.

4. The compound or salt according to claim 3 wherein X is N.

5. The compound or salt according to claim 4 wherein R is C1-C3 alkyl.

6. The compound or salt according to claim 5 of the formula:

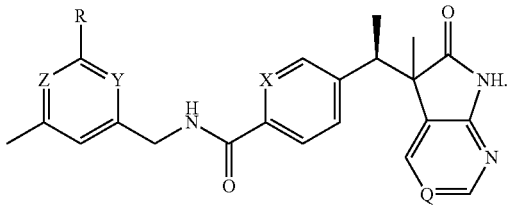

7. The compound or salt according to claim 6 of the formula:

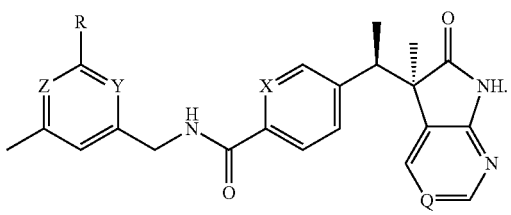

8. The compound or salt according to claim 1 wherein the compound is:

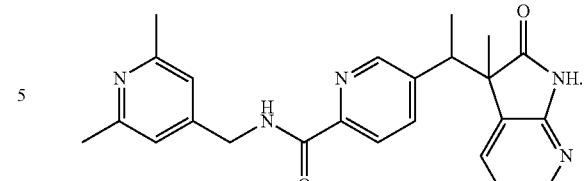

9. The compound or salt according to claim 8 wherein the compound is:

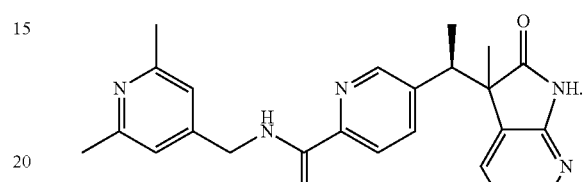

10. The compound or salt according to claim 9 wherein the compound is:

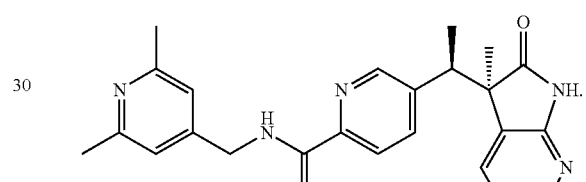

11. The salt according to claim 10 which is:

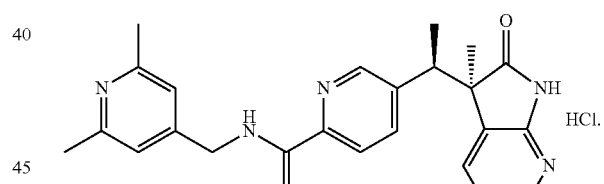

12. The salt according to claim 11 which is hydrated.

13. The salt according to claim 12 which is crystalline.

14. The salt according to claim 13 which is characterized by a substantial peak in the X-ray diffraction spectrum, at diffraction angle 2-theta of 20.7° in combination with one or more of the peaks selected from the group consisting of 19.8°, 12.9°, and 14.0°; with a tolerance for the diffraction angles of 0.2 degrees.

15. The salt according to claim 11 which is a methanolate.

16. The salt according to claim 15 which is crystalline.

17. The salt according to claim 16 which is characterized by a substantial peak in the X-ray diffraction spectrum, at diffraction angle 2-theta of 16.3° in combination with one or more of the peaks selected from the group consisting of 24.6°, 20.8°, and 20.1°, with a tolerance for the diffraction angles of 0.2 degrees.

18. A method of treating migraine in a patient, comprising administering to a patient in need thereof an effective amount of a compound or salt according to claim 1.

19. A method of preventing migraine in a patient, comprising administering to a patient in need thereof an effective amount of a compound or salt according to claim 1.

20. A method of treating migraine in a patient, comprising administering to a patient in need thereof an effective amount of a compound or salt according to claim 10.

21. A method of preventing migraine in a patient, comprising administering to a patient in need thereof an effective amount of a compound or salt according to claim 10.

22. A pharmaceutical composition, comprising a compound or salt according to claim 1 with one or more pharmaceutically acceptable carriers, diluents, or excipients.

23. A pharmaceutical composition, comprising a compound or salt according to claim 10 with one or more pharmaceutically acceptable carriers, diluents, or excipients.

24. A process for preparing a pharmaceutical composition, comprising admixing a compound or salt according to claim 1 with one or more pharmaceutically acceptable carriers, diluents, or excipients.

25. A process for preparing a pharmaceutical composition, comprising admixing a compound or salt according to claim 10 with one or more pharmaceutically acceptable carriers, diluents, or excipients.

* * * * *